(12) United States Patent
Bachellier

(10) Patent No.: US 11,117,107 B2
(45) Date of Patent: Sep. 14, 2021

(54) LOW SHEAR, LOW VELOCITY DIFFERENTIAL, IMPELLER HAVING A PROGRESSIVELY TAPERED HUB VOLUME WITH PERIODS FORMED INTO A BOTTOM SURFACE, SYSTEMS AND METHODS FOR SUSPENSION CELL CULTURING

(71) Applicant: Cellmotions Inc., Dundas (CA)

(72) Inventor: Carl R. Bachellier, Dundas (CA)

(73) Assignee: CELLMOTIONS INC.

( * ) Notice: Subject to any disclaimer, the term of this patent is extended or adjusted under 35 U.S.C. 154(b) by 399 days.

(21) Appl. No.: 16/169,354

(22) Filed: Oct. 24, 2018

(65) Prior Publication Data

US 2019/0054432 A1   Feb. 21, 2019

Related U.S. Application Data

(63) Continuation-in-part of application No. PCT/CA2017/050845, filed on Jul. 11, 2017.

(Continued)

(30) Foreign Application Priority Data

Jul. 18, 2016   (CA) ..................... 2936339

(51) Int. Cl.
*B01F 7/00*   (2006.01)
*B01F 7/16*   (2006.01)
(Continued)

(52) U.S. Cl.
CPC .......... *B01F 7/00375* (2013.01); *B01F 7/163* (2013.01); *B01F 7/22* (2013.01);
(Continued)

(58) Field of Classification Search
CPC ........ B01F 7/00375; B01F 7/163; B01F 7/22; C12M 27/02; C12M 27/06
See application file for complete search history.

(56) References Cited

U.S. PATENT DOCUMENTS 3,644,056 A  *  2/1972  Wiselius ............. F04D 29/2277
                                                        415/218.1
4,093,401 A  *  6/1978  Gravelle ............... F04D 29/284
                                                        415/143

(Continued)

FOREIGN PATENT DOCUMENTS

CA      2872355 A1      6/2015
GB      2486019 A  *   6/2012   ........... F04D 29/281

(Continued)

OTHER PUBLICATIONS

"Microcarrier Cell Culture Principles and Methods"; GE Healthcare Life Sciences Handbooks; 2005-2013 General Electric Company—First Published Apr. 2005; pp. 1-171.

(Continued)

*Primary Examiner* — Tony G Soohoo
(74) *Attorney, Agent, or Firm* — Sand, Sebolt & Wernow Co., LPA

(57) ABSTRACT

Disclosed is an impeller for mixing a fluid wherein the impeller is fashioned so as to substantially reduce areas of fluid acceleration and deceleration around a hub region of the impeller during fluid mixing. Additionally, a bioreactor system having microcarriers, kit of parts and cell culturing method are also provided. The impeller has a generally circularly shaped hub having a downwardly directed progressively tapered volume which has plurality of periods formed therein corresponding to the number of increasingly arced blades. Each of the increasingly arced blades flare outwards to a distal end region of the impeller and have an increasing radius to said arc towards a peripheral edge (Continued)

region of said hub. The flare to the increasingly arced blades defines a larger circumference than that of said hub, thereby imparting a generally frusto-conical shape to the impeller. A method mixing a fluid using the impeller disclosed herein is also disclosed.

16 Claims, 20 Drawing Sheets

Related U.S. Application Data

(60) Provisional application No. 62/577,933, filed on Oct. 27, 2017.

(51) Int. Cl.
| | | |
|---|---|---|
| *B01F 7/22* | (2006.01) | |
| *C12M 1/06* | (2006.01) | |
| *F04D 7/04* | (2006.01) | |
| *F04D 29/22* | (2006.01) | |
| *F04D 29/70* | (2006.01) | |
| *F04D 29/18* | (2006.01) | |
| *C12M 1/02* | (2006.01) | |
| *C12M 1/12* | (2006.01) | |

(52) U.S. Cl.
CPC .............. *C12M 27/06* (2013.01); *C12M 1/02* (2013.01); *C12M 25/16* (2013.01); *C12M 27/02* (2013.01); *F04D 7/045* (2013.01); *F04D 29/181* (2013.01); *F04D 29/2216* (2013.01); *F04D 29/708* (2013.01)

(56) References Cited

U.S. PATENT DOCUMENTS

| | | | | | |
|---|---|---|---|---|---|
| 4,468,358 | A | * | 8/1984 | Haegeman | B01F 3/04773 |
| | | | | | 261/91 |
| 4,594,052 | A | * | 6/1986 | Niskanen | F04D 7/045 |
| | | | | | 415/121.1 |
| 4,647,215 | A | * | 3/1987 | Armitage | B01F 7/00416 |
| | | | | | 366/266 |
| 5,314,310 | A | * | 5/1994 | Bachellier | B01F 7/00341 |
| | | | | | 366/265 |
| 5,938,332 | A | * | 8/1999 | Bachellier | B01F 7/001 |
| | | | | | 366/330.1 |
| 6,158,959 | A | * | 12/2000 | Arbeus | F04D 29/242 |
| | | | | | 415/204 |
| 7,597,541 | B2 | * | 10/2009 | White | F04D 29/282 |
| | | | | | 415/204 |
| 8,985,970 | B2 | * | 3/2015 | Spaggiari | F04D 29/329 |
| | | | | | 417/423.1 |
| 9,682,348 | B2 | * | 6/2017 | Bachellier | C10G 33/06 |
| 9,745,996 | B2 | * | 8/2017 | Nurzynski | F04D 17/06 |
| 9,863,423 | B2 | * | 1/2018 | Bachellier | F04D 13/08 |
| 9,868,155 | B2 | * | 1/2018 | Gerber | F04D 29/023 |
| 9,920,768 | B2 | * | 3/2018 | Bruss | F04D 29/281 |
| 10,247,195 | B2 | * | 4/2019 | Manninen | F04D 7/04 |
| 10,371,154 | B2 | * | 8/2019 | Jayaram | F04D 9/003 |
| 10,527,053 | B2 | * | 1/2020 | Xu | F04D 29/2277 |
| 10,550,854 | B2 | * | 2/2020 | Lorcher | B29C 45/26 |
| 2010/0061841 | A1 | * | 3/2010 | Visintainer | F04D 29/2261 |
| | | | | | 415/169.1 |
| 2010/0135765 | A1 | * | 6/2010 | Burgess | F04D 13/12 |
| | | | | | 415/1 |
| 2011/0194931 | A1 | * | 8/2011 | Swiatek | F04D 29/44 |
| | | | | | 415/206 |
| 2014/0349379 | A1 | * | 11/2014 | Bachellier | C10G 33/06 |
| | | | | | 435/257.1 |
| 2015/0292523 | A1 | * | 10/2015 | Bachellier | F04D 7/045 |
| | | | | | 416/223 R |
| 2017/0096628 | A1 | * | 4/2017 | Bachellier | B01F 7/00341 |
| 2018/0112673 | A1 | * | 4/2018 | Manninen | F04D 29/22 |
| 2019/0054432 | A1 | * | 2/2019 | Bachellier | B01F 7/00375 |

FOREIGN PATENT DOCUMENTS

| | | | | |
|---|---|---|---|---|
| GB | 2486019 | A | | 6/2012 |
| WO | 2011051880 | A3 | | 6/2011 |
| WO | 2013082717 | A1 | | 6/2013 |
| WO | 2015160850 | A1 | | 10/2015 |
| WO | WO-2015160850 | A1 | * 10/2015 | ............. F04D 13/08 |
| WO | WO-2016165795 | A1 | * 10/2016 | ......... F04D 29/2261 |

OTHER PUBLICATIONS

"Corning Synthemax II Microcarriers, Dissolvable, 5g, Sterile"; Corning Incorporated Life Sciences; Catalog No. 4988; 2018.
"Expansion and Characterization of Mesenchymal Stem Cells on Pall SoloHill Microcarriers"; Pall Life Sciences; 2015; pp. 1-12.
"Human Mesenchymal Stem Cell Growth on Corning Denatured Collagen Dissolvable Microcamers in a 5L Bioreactor"; Weber et al.; Oct. 2017; pp. 1-8.

* cited by examiner

LOW SHEAR, LOW VELOCITY DIFFERENTIAL, IMPELLER HAVING A PROGRESSIVELY TAPERED HUB VOLUME WITH PERIODS FORMED INTO A BOTTOM SURFACE, SYSTEMS AND METHODS FOR SUSPENSION CELL CULTURING

CROSS-REFERENCE TO RELATED APPLICATIONS

The present application is a U.S. Continuation-in-Part Patent Application of International Patent Application serial number PCT/CA2017/050845 entitled "LOW SHEAR, LOW VELOCITY DIFFERENTIAL, IMPELLER HAVING A PROGRESSIVELY TAPERED HUB VOLUME WITH PERIODS FORMED INTO A BOTTOM SURFACE", filed Jul. 11, 2017 which in turn claims the benefit of priority to Canadian Patent Application serial number 2,936,339 entitled "LOW SHEAR, LOW VELOCITY DIFFERENTIAL, IMPELLER HAVING A PROGRESSIVELY TAPERED HUB VOLUME WITH PERIODS FORMED INTO A BOTTOM SURFACE", filed Jul. 18, 2016, each of which is incorporated herein by reference in its entirety. The present application also claims the benefit of U.S. Provisional Patent Application Ser. No. 62/577,933 entitled "SYSTEM AND METHOD FOR SUSPENSION CELL CULTURING WITH BIODEGRADABLE MICROCARRIERS", filed Oct. 27, 2017, which is incorporated herein by reference in its entirety.

TECHNICAL FIELD

The present disclosure relates to an impeller for mixing fluids and a system utilizing impellers for suspension cell culturing with biodegradable and non-biodegradable microcarriers. In particular, the present disclosure relates to an impeller and system utilizing impellers for suspension cell culturing with biodegradable and non-biodegradable microcarriers for mixing fluids in a bioreactor vessel which requires a low-shear environment substantially free from zones of turbulent flow velocity differentials and maintaining laminar flow within for cell propagation.

BACKGROUND

Stem cell bioreactors and vaccine bioreactors are used to propagate and grow cells. Suspension culturing is a technique that is known to grow and propagate large numbers of cells, such as stem cells, as well as cells which are not easily cultured in petri dishes. Certain suspension cell culturing techniques may involve the use of microcarriers to increase available surface area for the cells to attach thereto during culturing; similar to that of culturing cells in a substrate-attached petri dish-cell culturing. In other suspension culturing techniques, the cells are cultured in a free-floating environment without the aid of microcarriers to which cells may attach. Accordingly, microcarriers are used as an attachment vehicle in cell culturing to increase the support area in which growing cells can attach.

As noted above, microcarriers are known for use in suspension cell culturing. For example, certain techniques have adopted the use of microcarriers which are typically 125 to 250 micrometer spheres comprised of a non-biodegradable material. Microcarriers, which are non-biodegradable can be made from glass, polystyrene and acrylamide, among other materials. The density of the material from which the microcarriers are comprised is generally selected such that the microcarriers remain in suspension, that being that they are neutrally buoyant in the culture medium and therefore only require gentle stirring for suspension cell culturing to remain in suspension. The generally neutral buoyancy of the microcarriers in the culture medium aids to decrease the amount of energy, or in other words, the vigorousness of stirring in order for the microcarriers to remain in suspension during culturing. This aids to decrease cell damage, and in some cases also to reduce cellular differentiation due to mechanical stresses. However, even with the generally neutrally buoyant microcarriers, cell differentiation due to mechanical stresses have been observed in certain cell In bioreactors which use microcarriers during suspension culturing, one of the first steps to successful propagation is cell attachment. Some cell varieties rely on a slight charge or cellular stickiness to attach to the microcarrier and/or to each other, and in a bioreactor, the fluid environment may be continuously mixed for purposes of even cell distribution, even gas gradients, even temperature and pH distributions. To maintain heterogeneity of the culture medium and that of the cell distribution, the fluid medium carrying the cells must be substantially constantly mixed. However, in many culture environments it is desirable, and often required that the medium flow be laminar and free from turbulent regions as well as velocity gradients within the dynamically moving culture medium. Providing a medium flow which is laminar and free from turbulent regions as well as velocity gradients promotes cell attachment and aids to prevent damage to the cells during culturing.

It is known that in the fluid flow and cellular suspension culturing fields that, that the fluid dynamics should adhere to strict parameters regarding velocity changes and stagnant zones so as to replicate an in vivo environment during in vitro culturing of cells as closely possible. Since suspension culturing inherently involves having the cells in motion during culturing, avoiding, or at least substantially reducing turbulence and zones of acceleration and deceleration within the bioreactor aids to simulate a substantially static in vivo growth environment.

In addition to the above-noted non-biodegradable microcarriers, biodegradable microcarriers are also available. For example, biodegradable microcarriers can be made from dextran, collagen, gelatin and alginate, among other materials. However, such biodegradable microcarriers generally have a higher relative density versus $H_2O$ as compared to certain non-biodegradable microcarriers, such as plastic or polystyrene and the like. In some instances, some non-biodegradable microcarriers also have a higher relative density versus $H_2O$ similar to that biodegradable microcarriers, such as for example greater than being neutrally buoyant. An example of a non-biodegradable microcarrier with a dextran coating is available from Sigma-Aldrich and is branded as Cytodex®, which has relative density of about 1.02 $cm^2/g$ versus $H_2O$. Therefore, under gentle stirring conditions, biodegradable microcarriers and non-biodegradable microcarriers having a higher relative density versus $H_2O$ as noted above, tend to remain settled in the bottom of a reactor vessel. Accordingly, in practice, in order to maintain such microcarriers having an increased relative density versus $H_2O$ in suspension during suspension cell culturing more vigorous stirring of the culture medium is required in order to maintain the such microcarriers in suspension. Such conditions can lead to cell damage and mechanical stresses, which in the case of stem cells, and indeed other cell types, may induce unwanted cell differentiation due to mechanical stresses. The effects of more vigorous suspension culturing medium velocity is further exacerbated as one scales up the bioreactor vessel size, such as from a one-litre suspension cell culture to, for example a fifty-litre suspension cell culture.

Although such microcarriers having an increased relative density versus H₂O may be used in larger scale suspension cell culturing, these microcarriers, in many applications such as in vivo implantation treatments, must be separated from the produced expanded cell cultures. This adds not only an addition step in the process, but can also lead to cell damage and thus produced cell number loss (reduces viable cell counts), as well as increase the risk of contamination of the produced cell culture. Such factors can ultimately increase the risk of infection, ineffective treatments and, with additional separation steps required, the cost of suspension cell culturing.

In many applications, it would be desirable to utilize biodegradable microcarriers to aid in suspension cell culturing techniques so as to ameliorate some of the possible complications of cell/microcarrier separation which may result with the use of non-biodegradable microcarriers.

Various impellers which are designed to mix fluids in a low shear environment and reduce turbulence may be suitable for use in suspension cell culturing. Examples of such impellers to stir culture media which may be used in bioreactors for suspension cell culturing have been described, for example in U.S. Pat. No. 5,314,310, entitled "SPIDER MOUNTED CENTRIFUGAL MIXING IMPELLER", issued May 24, 1994 (Bachellier, Carl R.), U.S. Pat. No. 5,938,332, entitled "MIXING DEVICE", issued Aug. 17, 1999 (Bachellier, Carl R.) and International Patent Application serial number PCT/CA2012/050873, entitled "IMPROVED IMPELLER APPARATUS AND DISPERSION METHOD FIELD OF THE INVENTION", filed Dec. 5, 2012 (Bachellier, Carl R.) disclose various impellers for mixing fluids which comprise a top hub having a flat interior surface; that is, the inside bottom surface of the hub is perpendicular to the axis of rotation. For example, the bottom surface of the hub, when the impeller is oriented in a vertical plane, is oriented horizontally. During use, when such impellers rotate, an upward spiral helical intake vortex to the fluid is created. This vortex collides with the flat surface, causing the vortex to compress and collapse on itself thereby creating an area of fluid deceleration and a turbulent region. In the upper part of these impellers, typically the top third, the fluid is discharged from the impeller at approximately a 90-degree angle to the axis of rotation, which disrupts the otherwise upward flow of fluid from the lower two thirds of the impeller. This can result in inadequate discharge to the exterior of the impeller of the fluid in approximately the upper third of the interior of the impeller, which then provides resistance to the fluid entering the bottom of the impeller (i.e. a backwash or stall effect), thereby impeding it from moving up to the hub. Thus, the fluid does not flow around and from the impeller in a smooth, substantially non-turbulent manner. In addition, particulates or other second phase materials, such as cells in a suspension culture, collide with the flat interior surface and may adhere to that surface in addition to colliding with one another in a detrimental fashion. This effect is exacerbated by the sharp interior angle where the upper edge of the blade attaches to the bottom surface of the hub.

International Patent Application serial number PCT/US2015/02580, entitled "CONICAL IMPELLER AND APPLICATIONS THEREOF", filed Apr. 14, 2015 (Bachellier, Carl R.) discloses a generally conically-shaped impeller for mixing fluids. The application, having the same inventor as the instant application, discloses a low shear impeller which has a hub with a conical surface extending into the interior of the impeller and a plurality spiral, or in other words, increasingly arced blades towards the outer peripheral are of the impeller. At the intersection of the conical surface and the spiral blades, during rotation in a fluid, this arrangement causes the fluid to form an upwardly swirling vortex in which entrained particles or gases are brought into the interior of the impeller and subsequently ejected from the impeller at a trailing edge of the spiral blades and along the trailing edge of the spiral blades. However, during testing and Computational Fluid Dynamics (CFD) modeling, it was discovered that at the conical surface of the hub, the fluid flow is turbulent, that being having zones of fluid acceleration and deceleration where the fluid becomes trapped in a recirculating flow pattern. It was discovered that the conical surface acts as a deceleration mechanism and in conjunction with the spiral blades creates a turbulent discharge.

Therefore, in certain applications the impeller of International Patent Application serial number PCT/US2015/025820 has drawbacks for certain applications of suspension cell culturing techniques. For example, the abovementioned impeller, during testing showed a significant deceleration of fluid at the apex of the interior conical surface by a factor of 190 times and a reacceleration of the fluid upon discharge. The impeller of International Patent Application serial number PCT/US2015/02580 also displayed a recirculatory eddy formation around the drive shaft assembly attachment point which may trap cells undergoing culturing into a zone which prevents even distribution to the rest of the colony growing in the bioreactor. Accordingly, although functional in many other applications, the fluid dynamic characteristics of the impeller disclosed in International Patent Application serial number PCT/US2015/02580 does not satisfactorily meet several of the needs for suspension cell propagation in bioreactors due to the inherent ultra-low stress requirements of certain cell types, in particular, stem cells.

It should be noted however, that, in the system and method for suspension cell culturing hereindescribed below, in certain applications of suspension cell culturing, the aforementioned impellers may by suitable for use with both biodegradable and non-biodegradable microcarriers.

It would be desirable, in some applications, to provide a scalable system and method for suspension cell culturing which uses biodegradable microcarriers and/or non-biodegradable microcarriers having a higher relative density versus H₂O, yet does not provide a higher shear and more turbulent environment to maintain the microcarriers in suspension. In other words, maintain a lower shear and less turbulent environment with culture medium velocities required to maintain the biodegradable microcarriers in suspension. Such a system and method may serve to reduce mechanical cell damage and unwanted cell differentiation with certain microcarriers as well as, in the case of biodegradable microcarriers, remove the need for a cell/microcarrier separation step known in systems which employ non-biodegradable microcarriers and also reduce factors known to lead to possible culture infection.

This background information is provided to reveal information believed by the applicant to be of possible relevance. No admission is necessarily intended, nor should it be construed, that any of the preceding information constitutes prior art.

SUMMARY

The following presents a simplified summary of the general inventive concepts described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

In light of the above background discussion it would desirable to develop an impeller for mixing fluid mediums and in particular fluid mediums for growing live cells or viruses in suspension culturing bioreactors for vaccine and stem cell production. Such an impeller may also aid in bioreactor devices for large-scale cell propagation purposes. In particular, it would be desirable to develop an impeller for mixing fluids which require a low-shear environment substantially free from zones of velocity differentials such as regions of acceleration and deceleration of the fluid medium as well as maintaining laminar flow around various areas of the impeller within a bioreactor vessel. The use of such an impeller which is substantially free from turbulent flow could allow scalable and healthy cell propagation in certain applications of suspension cell culturing.

Accordingly, need exists for system and method that may overcome some of the drawbacks of known techniques, or at least, provides a useful alternative thereto for suspension cell culturing utilizing biodegradable microcarriers and/or non-biodegradable microcarriers having a higher relative density versus $H_2O$. Some aspects of this disclosure provides examples of such a system and methods which utilizes cell culture bioreactors and low shear, low turbulence-generating impellers with biodegradable microcarriers and non-biodegradable microcarriers having a higher relative density versus $H_2O$, for example greater than being neutrally buoyant in $H_2O$.

It has been surprisingly discovered that by providing a hub to the impeller which has a downwardly directed progressively tapered volume interior to a proximal end region where an outer edge of the blades are coupled to the hub and the blades being further coupled to the downwardly directed progressively tapered volume in a decreasing arc, or in other words following a spiral helical pattern, inward to a predetermined point aids to produce a prewhirl to a fluid below the impeller as it is rotated.

The internal surface structure of the hub, the downwardly directed progressively tapered volume having the blades following along a corresponding period formed therein, acts to create as a prewhirl device which substantially matches the prewhirl generated by the circumferentially attached inwardly decreasingly arced blades. Swirling channels, the periods in some embodiments, intermittent the inwardly decreasingly arced blades allows the vortex created by the blades and motion of the hub to meet and be divided upwardly and outwardly with minimal velocity change to the various regions of the fluid about the hub. The swirling internal channels of the downwardly directed progressively tapered volume of the hub extend into discharge channels on the upper anterior side of the hub which provide a substantially smooth velocity transition of the fluid in various zones and reduce or substantially eliminate known zones of recirculation and turbulence associated with the above-discussed prior art. Additionally, the impeller described herein, unlike those of the abovementioned previously disclosed impellers, is substantially devoid of horizontal surfaces perpendicularly extending from the top of the hub near the rotatable drive attachment region which interrupts laminar flow of the fluid in and around various regions of the impeller.

In one aspect there is provided an impeller couplable to a rotatable drive by way of a rotatable drive attachment region coupled to a generally circularly shaped hub. The generally circularly shaped hub includes a downwardly directed progressively tapered volume having coupled thereto a proximal end region of one or more arced blades arranged along a periodic pattern formed into the downwardly directed progressively tapered volume wherein the number of periods corresponds to the number of blades. Each of the one or more arced blades has an increasing radius to the arc towards a peripheral edge region of the hub. The proximal end region of the one or more increasing radius arced blades extends from the peripheral edge region of the hub along the downwardly directed progressively tapered volume to a predetermined point inward of said peripheral edge region. Furthermore, each of the one or more arced blades is flared as it extends from the progressively tapered volume such that a distal end region of each of the one or more increasing radius arced blades, in combination, defines a larger circumference than that of the hub, thereby imparting a generally frusto-conical shape to the impeller.

In some embodiments, the impeller comprises at least two increasing radius arced blades.

In some embodiments, the periods formed into the downwardly directed progressively tapered volume comprise a plurality of spiral helices which corresponds the number of increasing radius arced blades.

In some embodiments, the one or more increasing radius arced blades extending from the peripheral edge region of the hub along the downwardly directed progressively tapered volume extend from ridges of the spiral helices.

In some embodiments, the downwardly directed progressively tapered volume has channels formed intermittent said ridges following the spiral helices so as to form a path continuous with a sequence of distinct conical spiral segments between the one or more increasing radius arced blades. In some embodiments, the channels have a substantially semicircular profile.

In some embodiments, the hub has a curved peripheral surface forming a discharge channel located at a peripheral terminus of the spiral helices adjacent to each of the one or more arced blade proximal end regions extending from the channels.

In some embodiments, the spiral helices of the downwardly directed progressively tapered volume are a logarithmic spiral.

In some embodiments of the impeller, the one or more increasing radius arced blades are integrally formed with said hub.

In some embodiments, the impeller further comprises a ring coupled near the distal end regions of the one or more increasing radius arced blades for connecting the one or more increasing radius arced blades. And, in further embodiments, the ring is integrally formed with the one or more increasing radius arced blades.

In some embodiments, the progressively tapered volume has a compound logarithmic taper.

In another aspect, there is provided an impeller couplable to a rotatable drive which comprises a generally circularly shaped hub including a downwardly directed progressively tapered volume having coupled thereto, toward a peripheral end region thereof, one or more flaring arced blades arranged along a periodic pattern formed into said downwardly directed progressively tapered volume to project generally downwards from said peripheral edge region and so as to define a periodically flaring impeller radius along their length which allows for tangential fluid flow between adjacent blade ends.

In some embodiments, the impeller comprises at least two flaring arced blades.

In some embodiments, the periods formed into the downwardly directed progressively tapered volume comprise a plurality of spiraling grooves each flowing toward a corresponding one of the arced blades.

In some embodiments, the spiraling grooves are defined by respective outer ridges and wherein each of the arced blades extends from a corresponding one of the outer ridges. Furthermore, in some embodiments, the spiraling grooves define helical channels that flow toward the adjacent blade ends. In some further embodiments, the spiraling grooves have a substantially semicircular profile.

In some embodiments, the spiraling grooves discharge between the adjacent blade ends.

In some embodiments, the spiraling grooves are logarithmically spiraling grooves.

In some embodiments, the one or more flaring arced blades are integrally formed with said hub.

In some embodiments, the impeller further comprises a ring coupled near the distal end region of the one or more flaring arced blades for connecting said one or more flaring arced blade ends. Furthermore, in some embodiments, the ring is integrally formed with said one or more flaring arced blades.

In some embodiments of the instant aspect, the progressively tapered volume has a compound logarithmic taper.

In yet another aspect, there is provided a method for mixing a fluid. The method comprising:
  introducing into a fluid an impeller coupled to a rotatable drive shaft;
  the impeller comprising a generally circularly shaped hub, including a downwardly directed progressively tapered volume having coupled thereto a proximal end region of one or more arced blades arranged along a periodic pattern formed into the downwardly directed progressively tapered volume wherein the number of periods corresponds to the number of blades;
  each of the one or more arced blades having an increasing radius to the arc towards a peripheral edge region of said hub;
  the proximal end region of the at one or more increasing radius arced blades extending from the peripheral edge region of the hub along the downwardly directed progressively tapered volume to a predetermined point inward of the peripheral edge region;
  the one or more arced blades further being flared as extending from the progressively tapered volume such that a distal end region of each of the one or more increasing radius arced blades, in combination, defines a larger circumference than that of the hub, thereby imparting a generally frusto-conical shape to the impeller;
  causing the impeller to rotate in the direction of the predetermined point inward of the peripheral edge region;
  by rotating of the impeller, creating a fluid vortex channeled upwards to a centre point of the progressively tapered volume so as to create a prewhirl to the fluid about a region near the hub, the velocity of which substantially matching the velocity of the fluid moving near the increasingly arced blades; and
  tangentially discharging the fluid between adjacent ends of the one or more increasingly arced blades so as mix the fluid.

In still yet another aspect, there is provided a method for mixing a fluid. The method comprising:
  introducing into a fluid an impeller coupled to a rotatable drive shaft;
  the impeller comprising a generally circularly shaped hub including a downwardly directed progressively tapered volume having coupled thereto toward a peripheral end region thereof one or more flaring arced blades arranged along a periodic pattern formed into the downwardly directed progressively tapered volume to project generally downwards from the peripheral edge region and to define a periodically flaring impeller radius along their length which allows for tangential fluid flow between adjacent blade ends;
  rotating of the impeller so as to create a fluid vortex channeled upwards to a centre point of the progressively tapered volume so as to create a prewhirl to the fluid about a region near the hub, the velocity of which substantially matching the velocity of the fluid moving near the one or more flaring arced blades; and tangentially discharging the fluid between adjacent ends of said one or more flaring arced blades so as mix the fluid.

In some embodiments of the above methods, the impeller includes at least two arced blades.

In some embodiments of the above methods, the periods formed into the downwardly directed progressively tapered volume comprise a plurality of spiral helices.

In some embodiments of the above methods, the arced blades extend from ridges of the spiral helices.

In some embodiments of the above methods, the spiral helices are logarithmic spirals. And in further embodiments of the above methods the ridges define helical channels that flow toward the adjacent blade ends and provide a fluid travel path.

In some embodiments of the above methods, the progressively tapered volume has a compound logarithmic taper.

Furthermore, a need exists for system and method that may overcome some of the drawbacks of known techniques, or at least, provides a useful alternative thereto for suspension cell culturing utilizing biodegradable microcarriers and/or non-biodegradable microcarriers having a higher relative density versus $H_2O$. Some aspects of this disclosure provide examples of such a system and methods which utilizes cell culture bioreactors and low shear, low turbulence-generating impellers with biodegradable microcarriers and non-biodegradable microcarriers having a higher relative density versus $H_2O$, for example greater than being neutrally buoyant.

In accordance with one aspect, there is provided a system for suspension cell culturing comprising: a suspension cell culturing bioreactor vessel having disposed therein an impeller operably coupled to a selectively-reversible rotatable drive shaft driveable by a motor; a plurality of biodegradable microcarrier and/or non-biodegradable microcarrier beads, a suitable culture medium and a suitable quantity of culturable cells. The impeller being characterized in that during use, the impeller, when rotated, imparts sufficient motion to the culture medium to maintain the plurality of microcarrier beads in suspension in an environment substantially-free from mechanical stresses to the cultureable cells.

In some preferred exemplary embodiments, the impeller provides a low shear environment. Furthermore, in additional preferred embodiments, the impeller provides a low turbulence environment.

In some exemplary embodiments, the biodegradable microcarrier beads are dextran microcarrier beads, collagen microcarrier beads, gelatin microcarrier beads, alginate microcarrier beads. In some embodiments, the microcarrier beads are Cytodex® microcarrier beads. In some exemplary embodiments, the non-biodegradable microcarrier beads have a relative density versus $H_2O$ of greater than being neutrally buoyant. In preferred embodiments, the biodegradable microcarrier beads and/or non-biodegradable microcarrier beads have a relative density versus $H_2O$ of from about 1.01 $cm^2/g$ to about 1.3 $cm^2/g$. In more preferred embodiments, the biodegradable microcarrier beads and/or non-biodegradable microcarrier beads have a relative density versus $H_2O$ of from about 1.01 $cm^2/g$ to about 1.2 $cm^2/g$.

In some preferred exemplary embodiments, the culturable cells are stem cells.

In some embodiments, the system is provided as a pre-prepared system.

In some embodiments, the bioreactor vessel has a capacity of greater than one litre. In some embodiments, the bioreactor vessel has a capacity of about fifty litres, or greater. Furthermore, in some embodiments, the suitable culture medium provided is slightly less than the volumetric capacity of the bioreactor vessel.

In another aspect, there is provided a kit of parts for suspension cell culturing comprising: a suspension cell culturing bioreactor vessel, an impeller disposable within the bioreactor and operably couplable to a selectively-reversible rotatable drive shaft driveable by a motor for stirring a suitable culture medium; a plurality of biodegradable microcarrier and/or non-biodegradable microcarrier beads, the suitable culture medium and a suitable quantity of culturable cells. The impeller being characterized in that during use the impeller, when rotated, imparts sufficient motion to the suitable culture medium to maintain the plurality of biodegradable microcarrier beads and/or non-biodegradable microcarrier beads in suspension in an environment substantially-free from mechanical stresses to the cultureable cells.

In some embodiments of the kit of parts, the impeller provides a low shear environment. In some embodiments, the impeller provides a low turbulence environment.

In some embodiments of the kit of parts, the biodegradable microcarrier beads are dextran microcarrier beads, collagen microcarrier beads, gelatin microcarrier beads, alginate microcarrier beads. In some embodiments, the microcarrier beads are Cytodex® microcarrier beads. In some embodiments of the kit of parts, the non-biodegradable microcarrier beads have a relative density versus $H_2O$ of greater than being neutrally buoyant. In preferred embodiments, the biodegradable microcarrier beads and/or non-biodegradable microcarrier beads have a relative density versus $H_2O$ of from about 1.01 $cm^2/g$ to about 1.3 $cm^2/g$. In more preferred embodiments, the biodegradable microcarrier beads and/or non-biodegradable microcarrier beads have a relative density versus $H_2O$ of from about 1.01 $cm^2/g$ to about 1.2 $cm^2/g$.

In some preferred exemplary embodiments of the kit of parts, the culturable cells are stem cells.

In some exemplary embodiments of the kit of parts, the bioreactor vessel has a capacity of greater than one litre. In some embodiments, the bioreactor vessel has a capacity of about fifty litres, or greater.

In some embodiments of the kit of parts, volume of the suitable culture medium provided is slightly less than the volumetric capacity of the bioreactor vessel.

In yet another aspect, there is provided a method for suspension cell culturing. The method comprising:
providing a suspension cell culturing bioreactor vessel having disposed therein an impeller for stirring a culture medium operably coupled to a selectively-reversible rotatable drive shaft driveable by a motor; the impeller characterized in that during use the impeller, when rotated, imparts sufficient motion to the culture medium contained with the bioreactor vessel to maintain a plurality of biodegradable microcarrier and/or non-biodegradable microcarrier beads in suspension in an environment substantially-free from mechanical stresses to the cultureable cells;

providing the plurality of biodegradable microcarrier and/or non-biodegradable microcarrier beads and introducing the plurality of biodegradable microcarrier and/or non-biodegradable microcarrier beads into the bioreactor;

providing the suitable culture medium and the suitable quantity of culturable cells;

providing suitable conditions for culturing the culturable cells; and culturing the culturable cells.

In some preferred embodiments of the method, the impeller provides a low shear environment. In some additionally preferred embodiments of the method, the impeller provides a low turbulence environment.

In some exemplary embodiments of the method, the biodegradable microcarrier beads are provided as dextran microcarrier beads, collagen microcarrier beads, gelatin microcarrier beads, alginate microcarrier beads. In some embodiments, the microcarrier beads are Cytodex® microcarrier beads. In some embodiments of the method, the non-biodegradable microcarrier beads have a relative density versus $H_2O$ of greater than being neutrally buoyant. In preferred embodiments, the biodegradable microcarrier beads and/or non-biodegradable microcarrier beads have a relative density versus $H_2O$ of from about 1.01 $cm^2/g$ to about 1.3 $cm^2/g$. In more preferred embodiments, the biodegradable microcarrier beads and/or non-biodegradable microcarrier beads have a relative density versus $H_2O$ of from about 1.01 $cm^2/g$ to about 1.2 $cm^2/g$.

In some preferred exemplary embodiments of the method, the culturable cells are provided as stem cells.

In some embodiments of the method, the provided bioreactor vessel has a capacity of greater than one litre. In some embodiments of the method, the provided bioreactor vessel has a capacity of about fifty litres, or greater.

In some embodiments of the method, the provided suitable culture medium is slightly less than the volumetric capacity of the bioreactor vessel.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

In order that the invention may be better understood, exemplary embodiments will now be described by way of example only, with references to the accompanying drawings, wherein.

DETAILED DESCRIPTION

With reference to the disclosure herein and the appended figures, an impeller 10 in accordance with various embodiments of the invention is described below. Additionally, the systems, methods and kit of parts described herein provide, in accordance with different embodiments, different examples in which low shear, low turbulence-generating impellers, including those noted above and the impeller 10 described in detail below, may be used with biodegradable and/or non-biodegradable microcarriers 54 for suspension cell culturing. Although it is contemplated that such a system can be utilized with several different cell types, the present system and method is generally provided for use in stem cell suspension culturing. Since it is contemplated that the presently described systems and method could be used to grow many different cell types in suspension culture, even though the present disclosure is directed to stem cells or, in some instances T-cells, it should not be limited to strictly stem cell suspension cell culturing.

Figure 1:
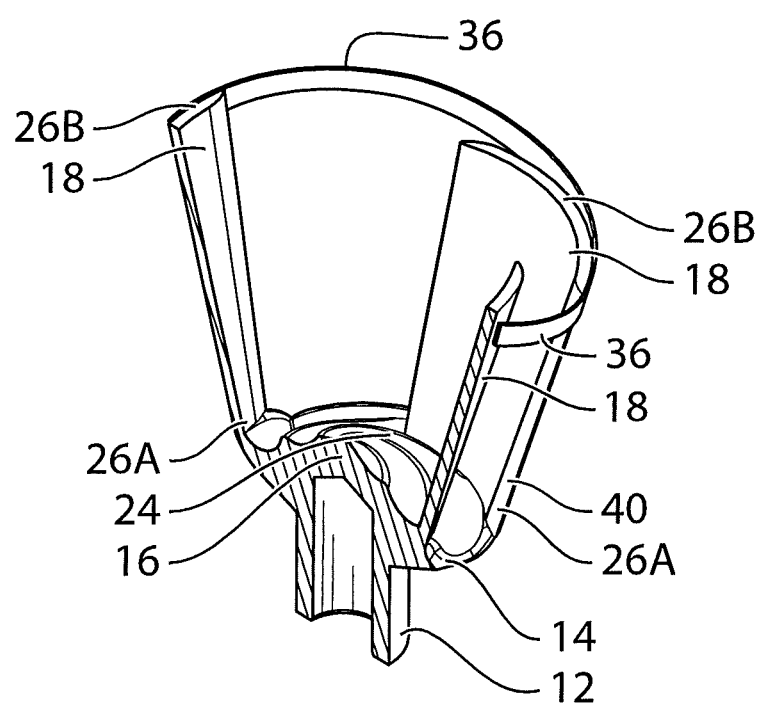
FIG. 1 is a cut-away perspective view along line A' of FIG. 5 of an embodiment of the impeller of the instant disclosure.
Figure 2:
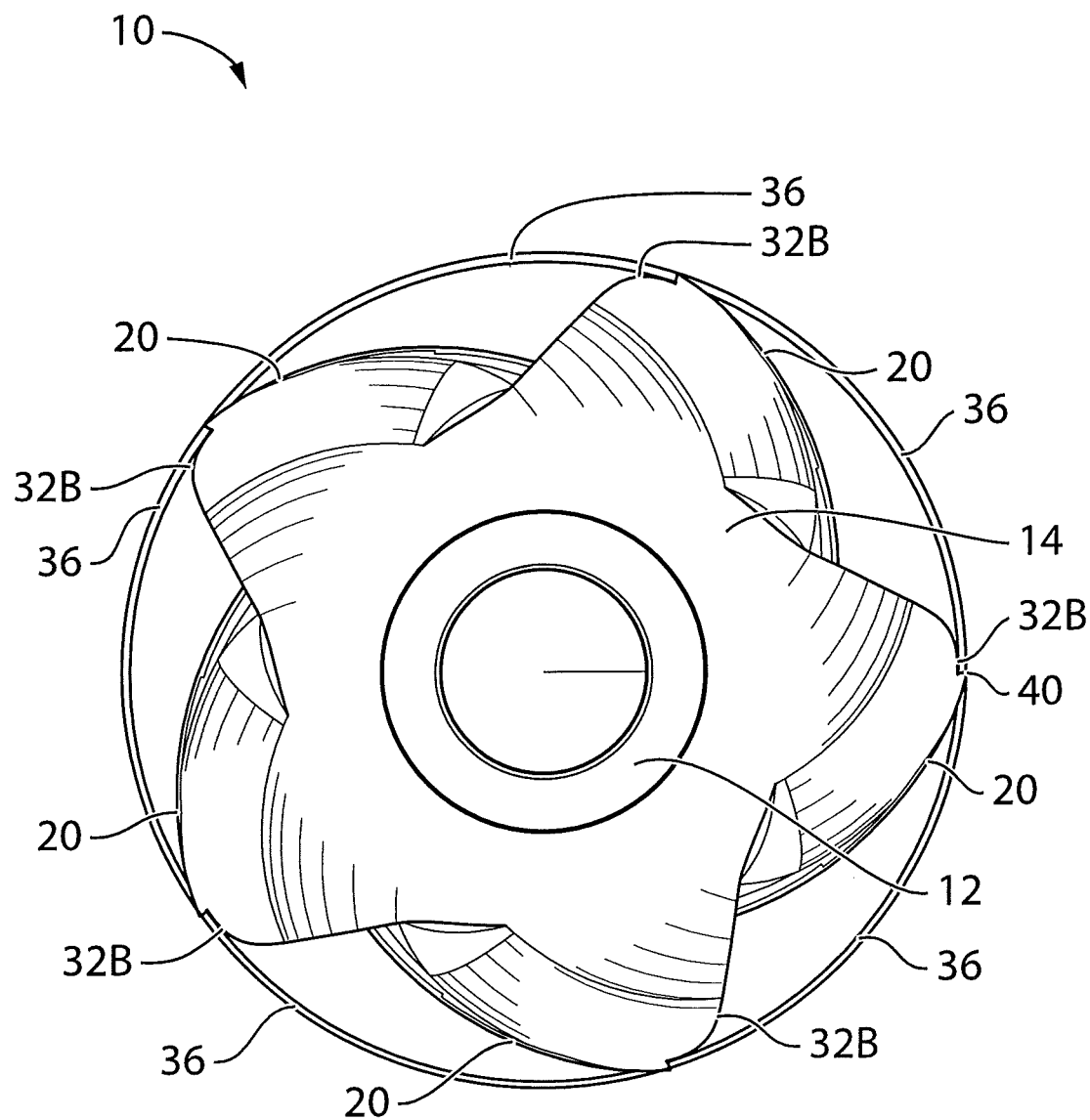
FIG. 2 is a top plan view of the impeller or FIG. 1.
Figure 14:
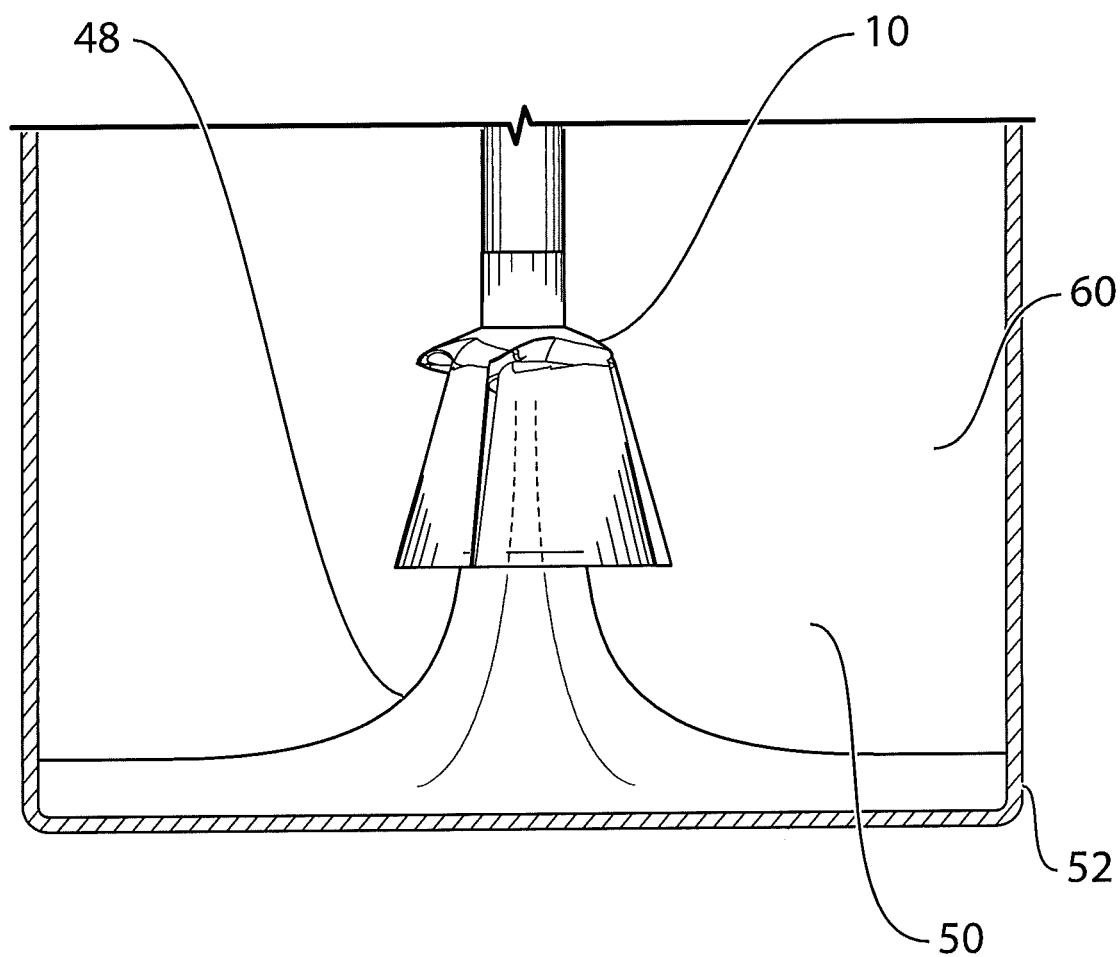
FIG. 14 is schematic side view of an impeller of the instant disclosure mixing a fluid showing the center vortex being drawn upwards into the downwardly directed progressively tapered volume.

With reference to FIG. 1, there is shown an embodiment of the impeller 10 of the instant disclosure. The impeller 10 has a rotatable drive attachment region 12 coupled to a generally circular shaped hub 14, as shown, for example, in FIGS. 1, 2 and 3, where the rotatable drive attachment region 12 is adapted for coupling to a rotatable drive member (not shown). With the impeller 10 coupled to a rotatable drive member via the rotatable drive attachment region 12, for example the drive shaft 56 of a motor 58, the impeller 10 is rotated as the drive shaft is turned. When immersed in a fluid or culture medium 62, the rotation of the impeller 10 results in the fluid being moved in a circular pattern so as to result in mixing of the fluid, as shown in FIG. 14, for example.

Figure 10:
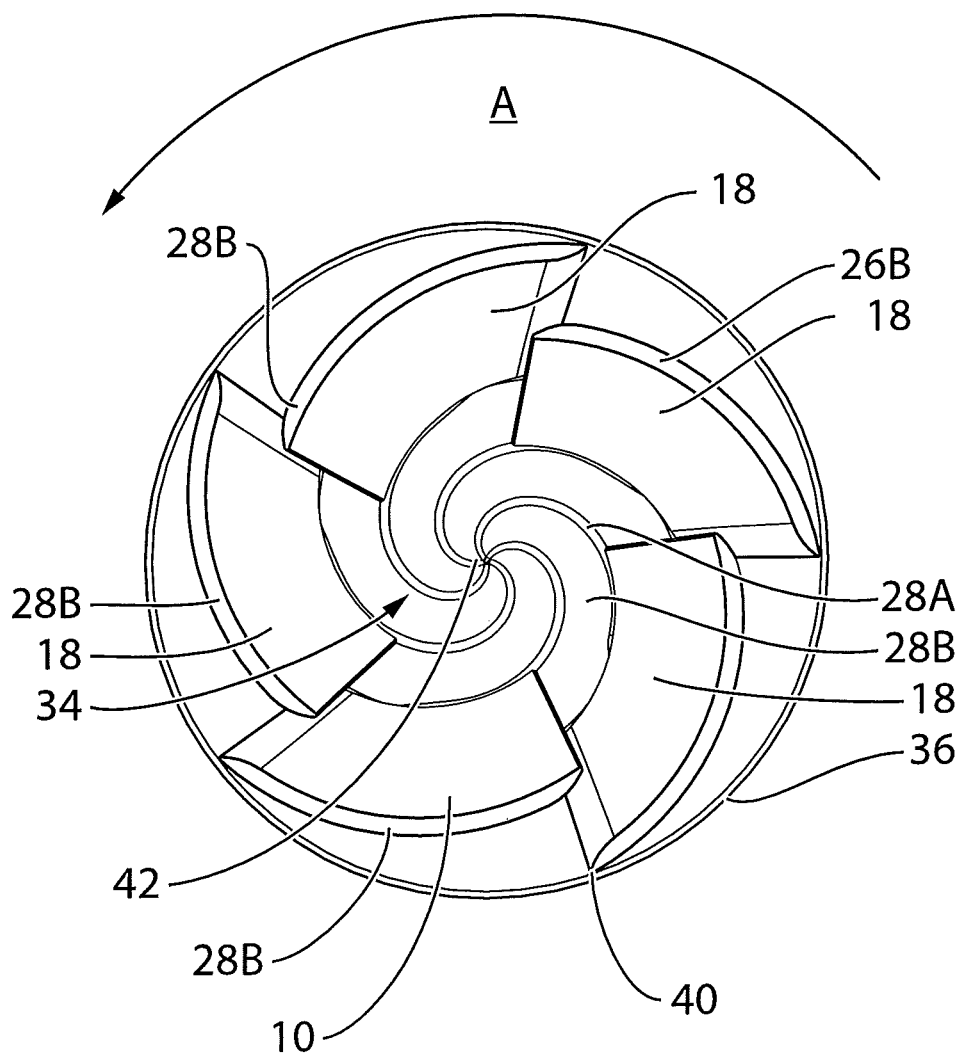
FIG. 10 is a bottom plan view of the impeller of FIG. 1.

The impeller 10, with reference to the figures, has a generally circularly shaped hub 14 with the rotatable drive attachment region 12 coupled to a top side thereof and depending from a bottom side thereof, a downwardly directed progressively tapered volume 16. There is at least one, and in most embodiments, a plurality of increasingly arced blades 18 arranged along a periodic pattern formed into the downwardly directed progressively tapered volume 16. The number of periods corresponds to the number of increasingly arced blades 18, for example, as shown in FIG. 10, five increasingly arced blades 18. As noted above, in some embodiments, not shown in the figures, the impeller 10 may be provided with only one blade 18, which, in such a case may follow a single helical period formed into the downwardly directed progressively tapered volume 16 such that the single blade 18 extends helically substantially around the hub 14 thus providing the required balance as the impeller 10 is rotated during use. In other embodiments, the single blade may be offset by counterbalance weight.

The increasingly arced blades 18 are coupled to the generally circularly shaped hub 14 at a proximal region 26a. The proximal region 26a of the blades extend from a peripheral edge region 20 of the hub 14 along the downwardly directed progressively tapered volume 16 to a predetermined point inward 24 of said peripheral edge region 20.

Figure 3:
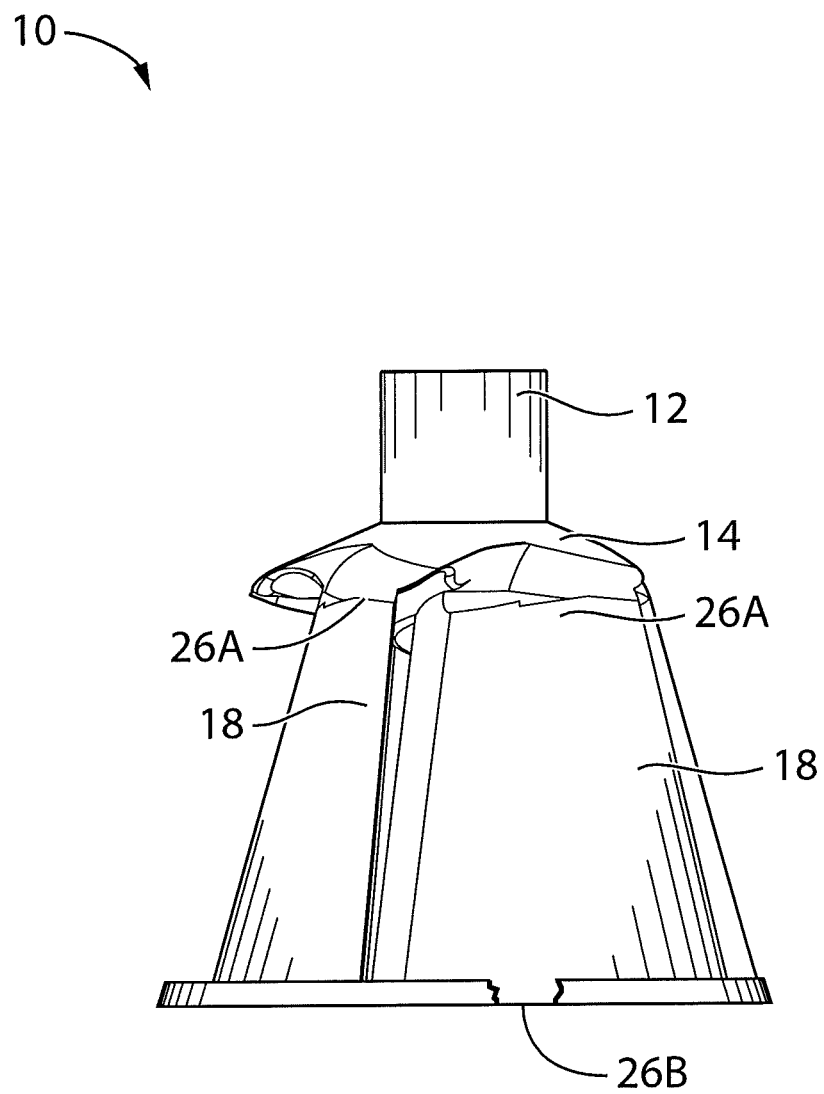
FIG. 3 is a side view of the impeller of FIG. 1.
Figure 4:
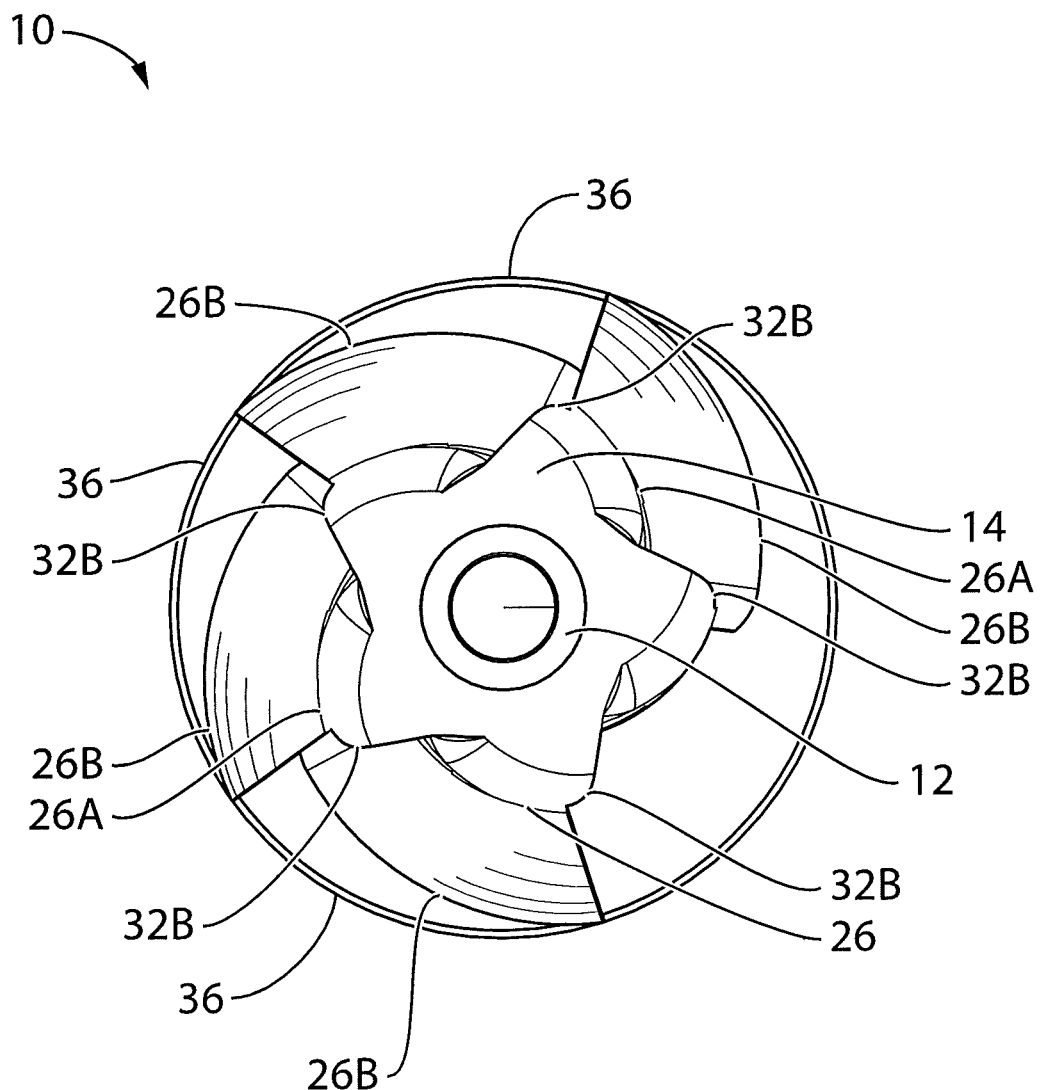
FIG. 4 is a top perspective view of the impeller of FIG. 1.

Turning now to FIG. 3, it is shown that the increasingly arced blades 18 are flared as they extend from the progressively tapered volume 16 to a distal end region 26b of the blades 18. In doing so the circumference of the impeller 10, as defined by the distal end regions 26b of the blades 18 is larger than the circumference of the hub 14 thereby imparting a generally frusto-conical, or flaring, shape to the impeller 10. As more clearly seen in the top plan view of FIG. 4, there is shown that the distal end regions 26b of the blades define a larger circumference to the impeller 10 in this distal area than near the hub 14. Thus, in other words, it can be said that the blades 18 are flared outwardly as they go from the peripheral end region 26a, coupled to the hub 14, to the distal end region 26b.

Figure 5:
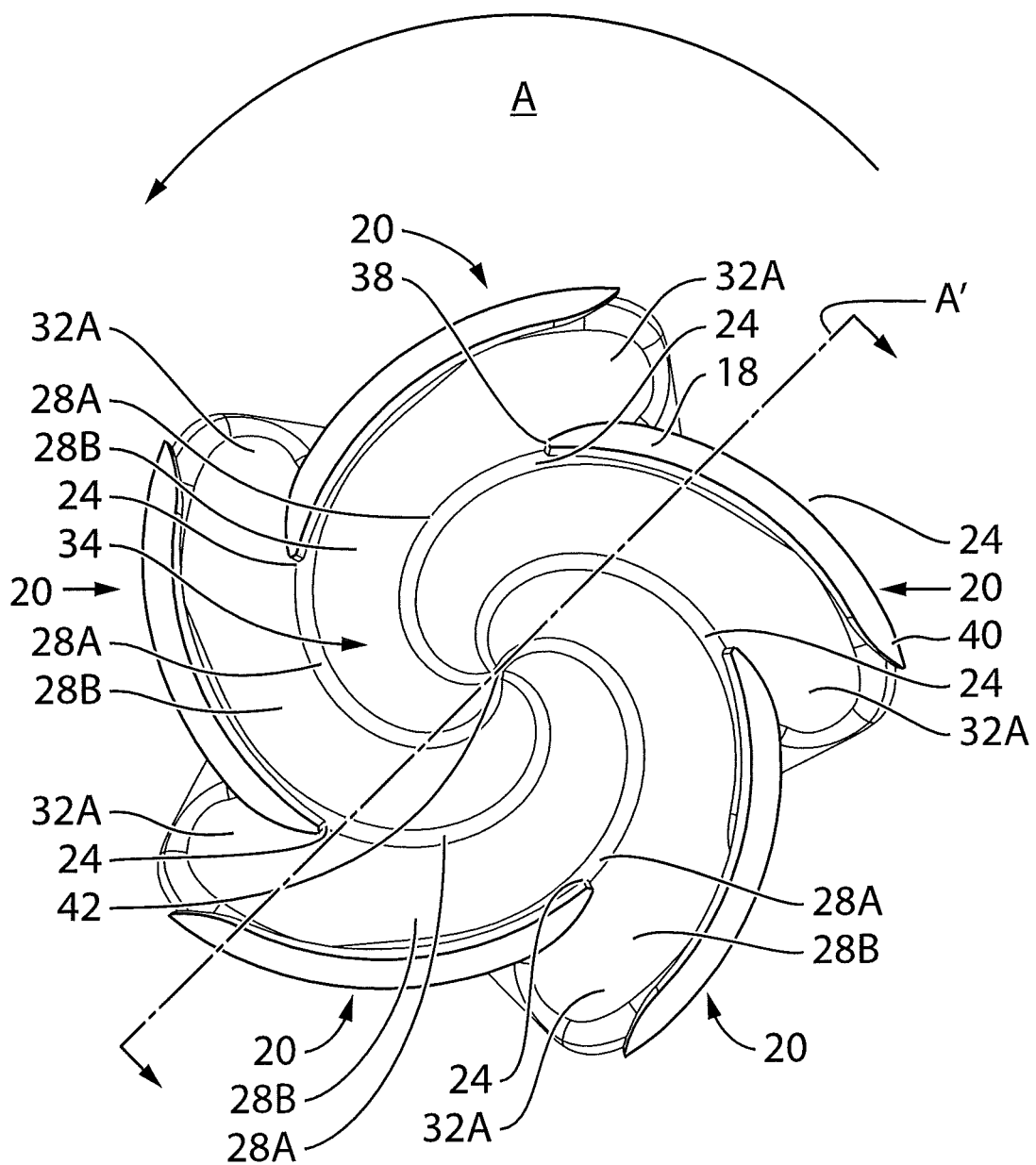
FIG. 5 is a bottom plan view of the impeller of FIG. 1.

Arrow "A" of FIGS. 5 and 10 shows the direction of rotation of the impeller 10 in use to mix a fluid 50. During rotation of the impeller 10, a leading edge region 38 of the blades 18 is moved though the fluid 50 and the fluid is ejected or discharged, in part, from the trailing edge region 40 of the blades 18 thereby aiding to circulate the fluid 50 in a vessel (not shown), in a manner as shown in FIG. 14, for example.

Figure 11:
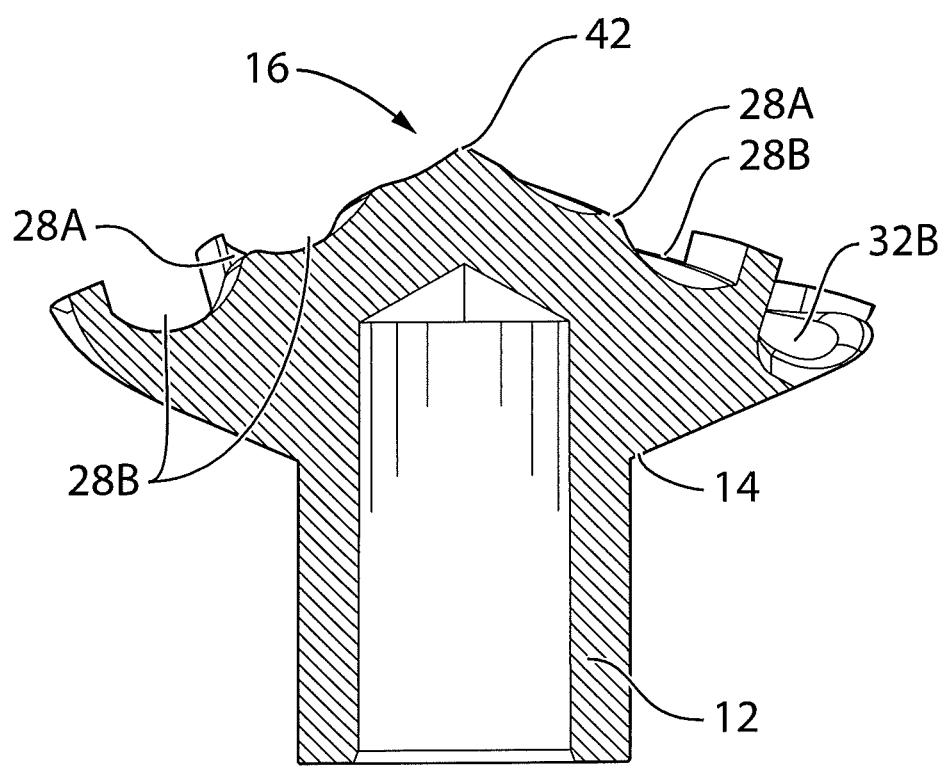
FIG. 11 is a cutaway side view along line A' of FIG. 5 of the rotatable drive attachment region, the generally circularly shaped hub and the downwardly directed progressively tapered volume with the blades removed of the impeller of FIG. 1.
Figure 12:
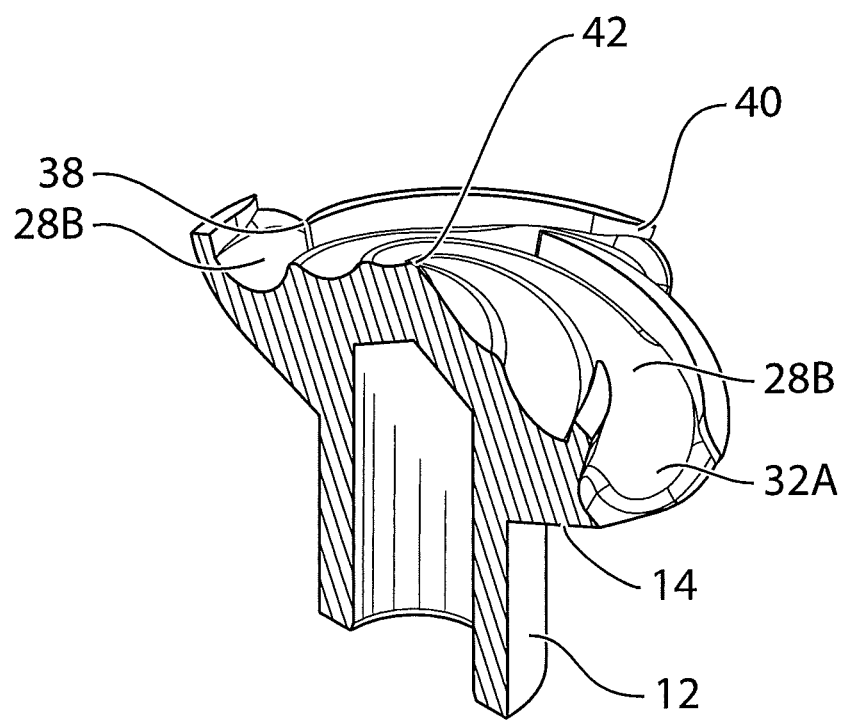
FIG. 12 is a cutaway perspective view along line A' of FIG. 5 of the rotatable drive attachment region, the generally circularly shaped hub and the downwardly directed progressively tapered volume with the blades removed of the impeller of FIG. 1.

Turing now to the bottom plan view of the impeller 10 shown in FIG. 5, the periods of the downwardly directed progressively tapered volume 16 may take the form of, in some embodiments, a plurality of spiral helices 34 formed into the downwardly directed progressively tapered volume 16. For example, each spiral helix 34 is formed by a single period. The number of spiral helices 34 corresponds to the number of periods of the hub and thus also the number of increasing radius arced blades 18. The periods or spiral helices 34 begin at the centre of the progressively tapered, at point referred to herein as the progressively tapered volume centre 42. Furthermore, the periods or spiral helices 34, extending from the progressively tapered volume centre 42, have a ridge component, the spiral ridges 28a and channel component, the spiral channels or spiraling grooves, 28b, thus forming a corresponding period. It should be noted that in some embodiments, (not shown) that the periods may be a raised formation, as opposed to, for example, the channel. FIGS. 11 and 12, are side cross-sectional views of the downwardly directed progressively tapered volume 16 and the rotatable drive attachment region 12 along line A' of FIG. 5. In these views, the spiral helices 34 and corresponding spiral ridges 28a and the spiral channels 28b can be seen. In some embodiments, the spiral channels 28b have a semi-circular profiles, as can be seen in the embodiment shown in figures.

Figure 6A:
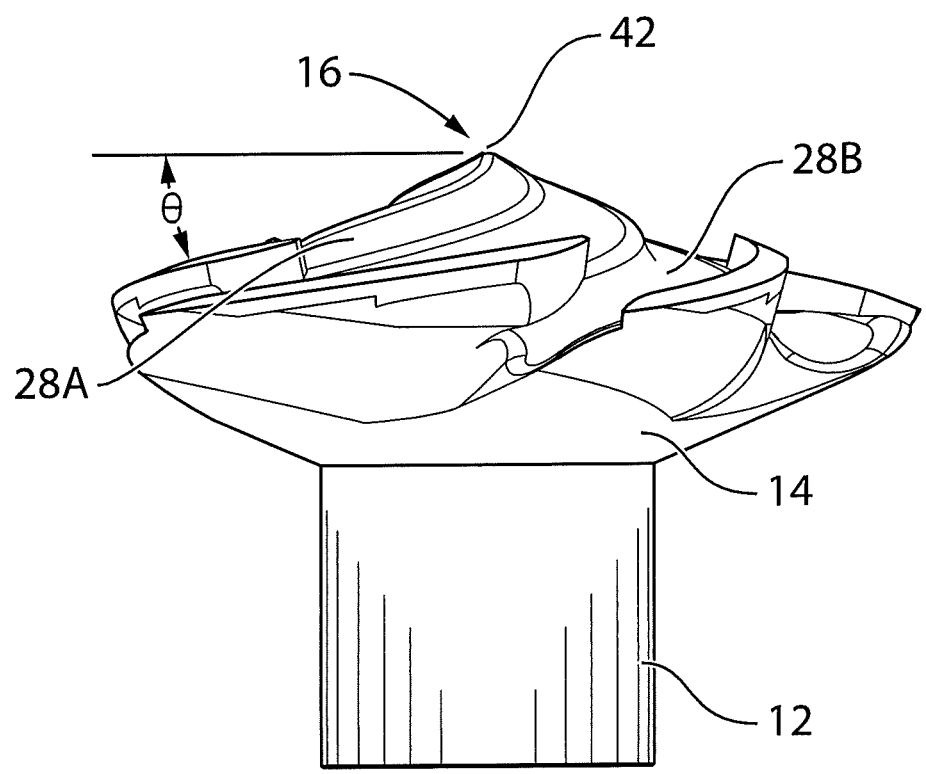
FIG. 6a is a side view of the rotatable drive attachment region, the generally circularly shaped hub and the downwardly directed progressively tapered volume with the blades removed of the impeller of FIG. 1.
Figure 6B:
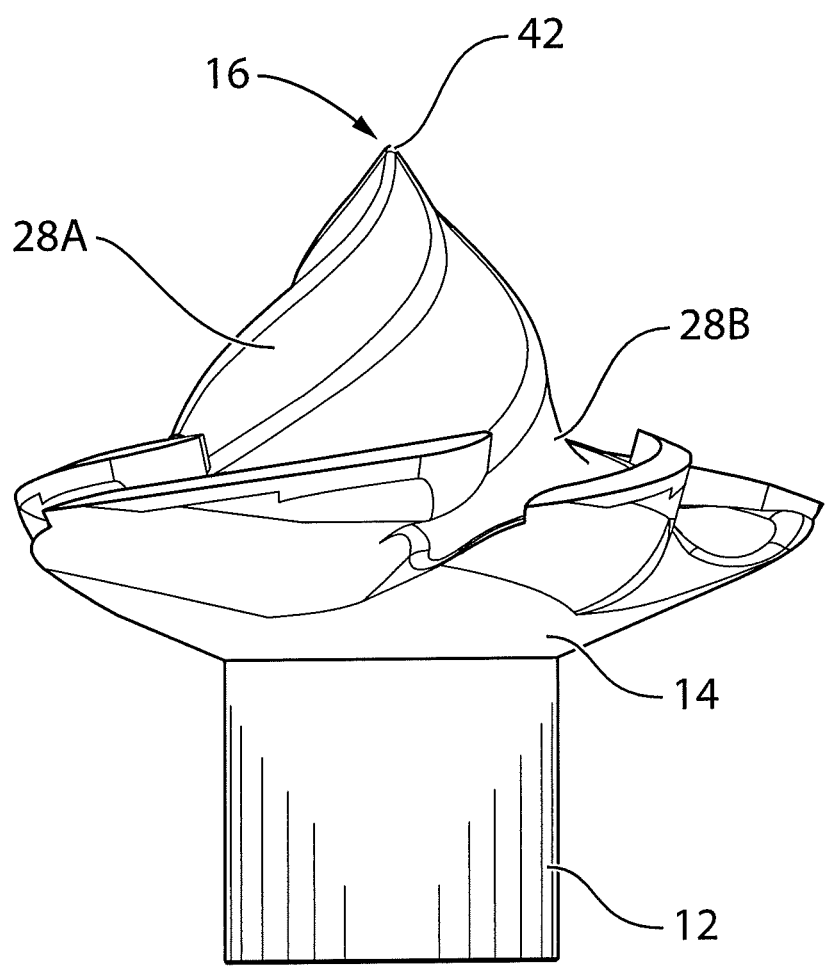
FIG. 6b is a side view of the rotatable drive attachment region, the generally circularly shaped hub and the downwardly directed progressively tapered volume with the blades removed of an embodiment of the impeller in accordance with the disclosure wherein the downwardly directed progressively tapered volume has logarithmic taper.
Figure 7:
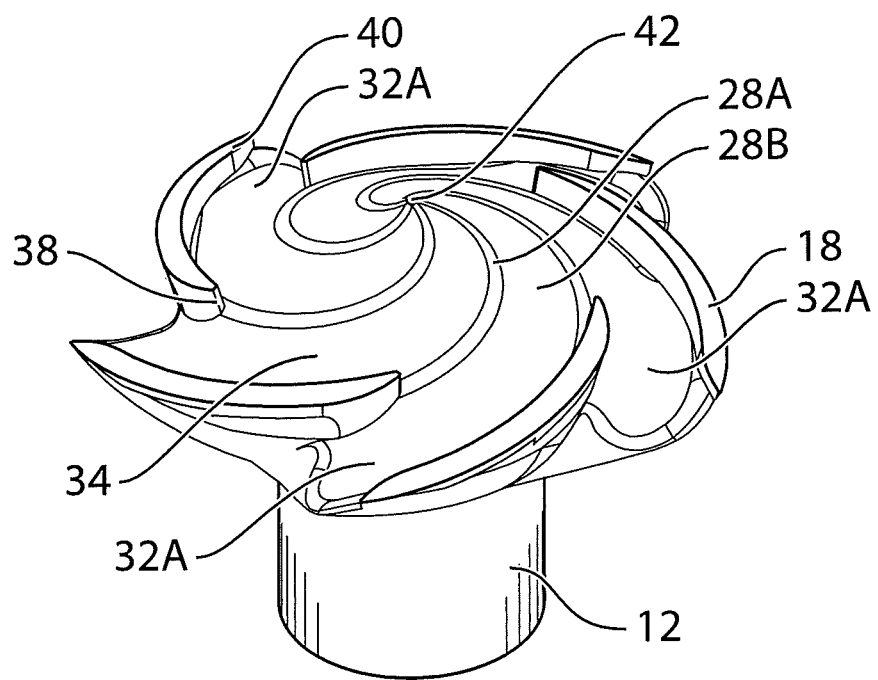
FIG. 7 is a side perspective view of the embodiment of FIG. 1 showing the rotatable drive attachment region, the generally circularly shaped hub and the downwardly directed progressively tapered volume with the blades removed.
Figure 8:
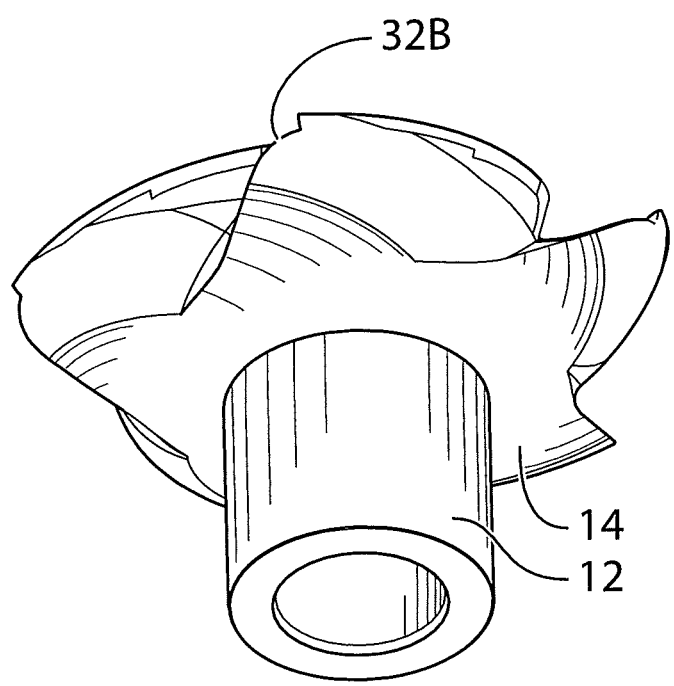
FIG. 8 is a top perspective view of the embodiment of FIG. 1 showing the rotatable drive attachment region and the generally circularly shaped hub with the blades removed.
Figure 9:
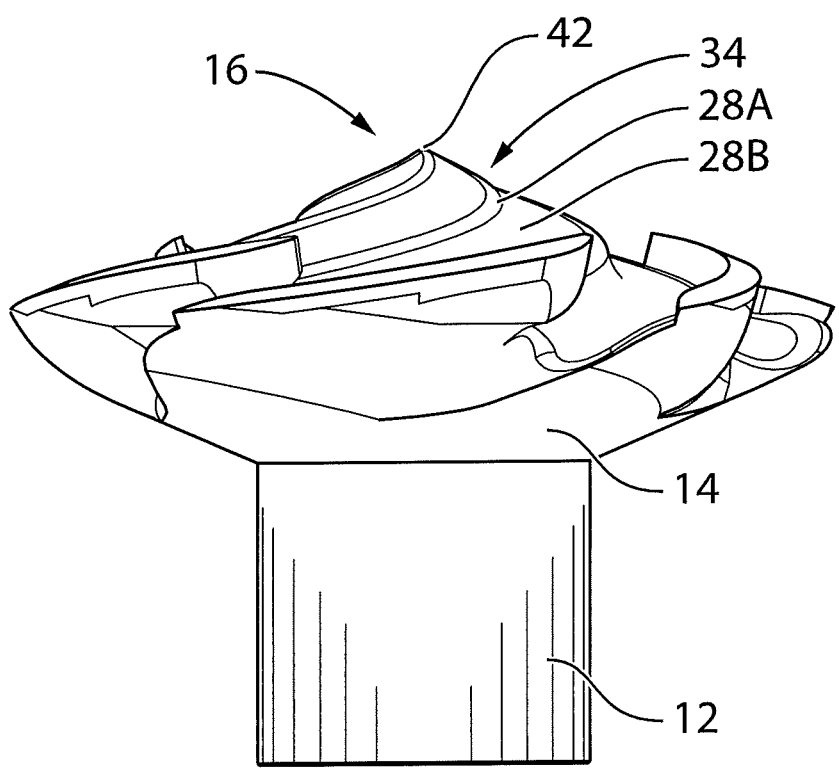
FIG. 9 is a side view of the rotatable drive attachment region, the generally circularly shaped hub and the downwardly directed progressively tapered volume with the blades removed of the impeller of FIG. 1.

With respect to the progressively tapered volume 16, in some embodiments it is provided as having a generally conical shape having the spiral ridges 26a and spiral 26b formed in its surface. In such an embodiment, the slope to the conical volume may have angle □, as shown for example in FIG. 6a. However, in other embodiments, the progressively tapered volume 16 may have a profile such that a cross-sectional profile of progressively tapered volume 16 is not seen as a straight line from the progressively tapered volume centre 42 to the outer peripheral region near the hub 14. That being, in some embodiments, the progressively tapered volume 16 may have a curved profile and furthermore, an exponentially increasing curve, or in other words a compound logarithmic taper to the volume 16, as shown for example, in FIG. 6b.

In some embodiments, the spiral component, formed by the spiral ridges 28a is provided as a logarithmic spiral. The logarithmic spiral pattern as formed on the surface of the progressively tapered volume 16 aids to create the above-noted prewhirl effect along a downward path extending from the progressively tapered volume centre 42 which matches a prewhirl generated by the circumferentially attached increasingly arced blades. The spiral channels 28b, or in other words, the swirling channels intermittent the increasingly arced blades allows the vortex created by the blades and motion of the hub to meet and be divided upwardly and outwardly with minimal velocity change to the various regions of the fluid about the hub 14. The swirling internal channels 28b of the downwardly directed progressively tapered volume of the hub extended into discharge channels 32a on the upper anterior side of the hub which provide a substantially smooth velocity transition of the fluid in various zones and reduce or substantially eliminate known zones of recirculation as the fluid tangentially flows between adjacent blade ends.

Furthermore, with respect to a height and a depth of the spiral ridges 26a and the spiral channels 26b, these may be variable. For example, one of skill in the art may wish to increase the depth of the spiral channels 26b in certain applications and decrease it in others. Additionally, in some embodiments, the depth of the spiral channels 26b may be increased or decreased along a spiral path from the progressively tapered volume centre 42 to the discharge channels 32b near the peripheral region of the hub 14.

Figure 13:
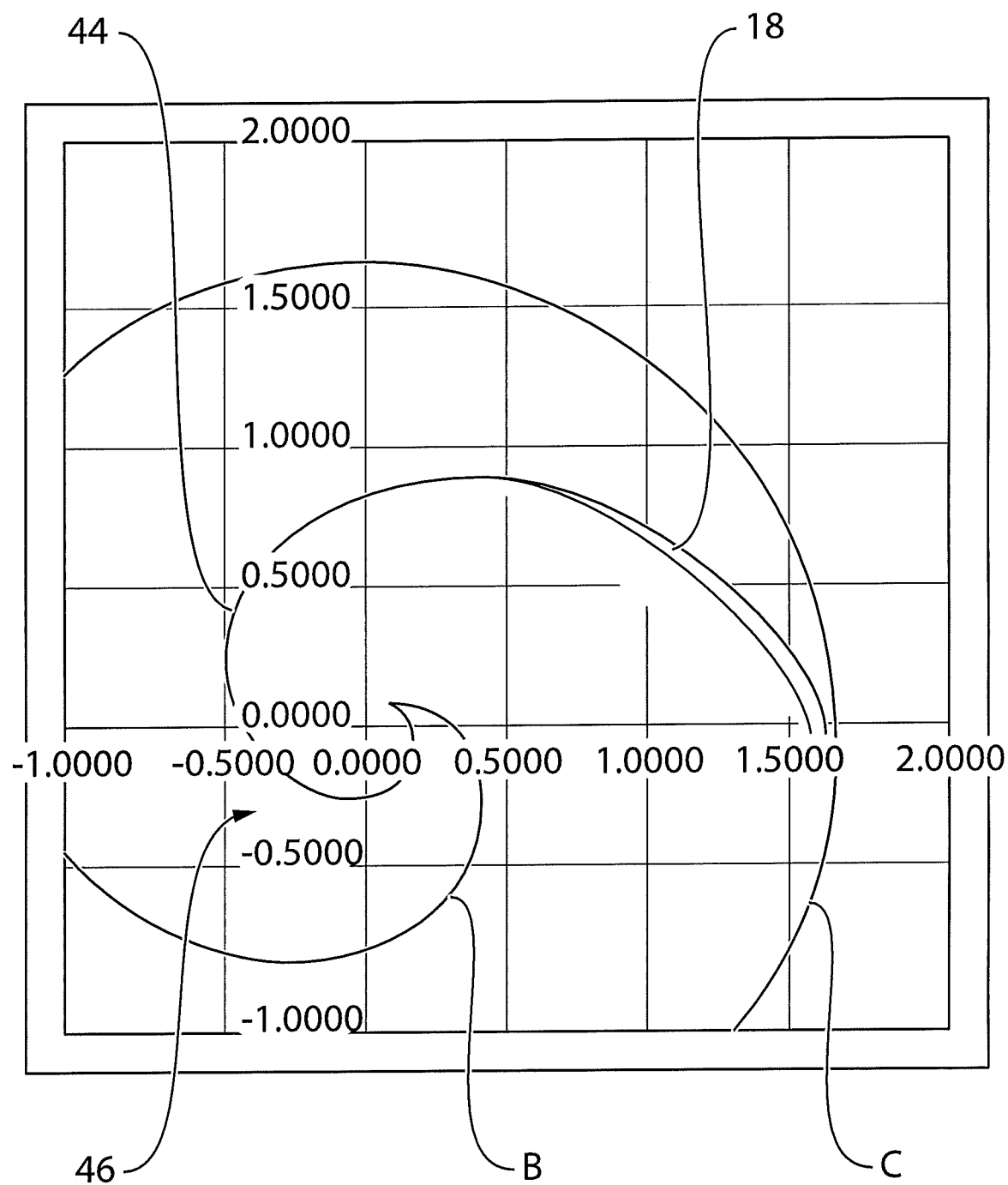
FIG. 13 is a graphical representation of a spiral having the general profile of a blade of the impeller of an embodiment of the instant application laid there-over.

Turning now to FIG. 13, with reference to the terminology of the increasing arced blade, a logarithmic spiral is shown. The spiral ridges 28a are formed along, for example, with reference to FIG. 13, line "B". As one looks toward the peripheral region 44 of the spiral 46, it can be noted that the spiral expands. Therefore, as the blades follow this profile, the arc or radius to the blades 18 increases towards the peripheral region 20 of the hub 14; hence arc to the blades can be defined as an increasing radius. For the purposes of reference, line "C" is provided so as to show schematic reference to the peripheral edge region 20 of the generally circularly shaped hub 14. Therefore, the logarithmic spiral path of the spiral ridges 28a is shown by line B over-layed and reference to the peripheral edge path of the generally circularly shaped hub 14 by line C.

During rotation of the impeller 10 in a fluid, the fluid 46 in a vessel is drawn upward into the impeller 10 as a center vortex 48, as shown in FIG. 14 towards the progressively tapered volume centre 42. The spiral ridges 28a and the spiral channels 28b create a prewhirl effect to the fluid. The fluid is drawn into the downwardly directed progressively tapered volume centre 42 and then travels along spiral channels 28b and then forwarded to the peripheral edge region 20 where is it ejected or discharged from the hub region via discharge channels 32. At the peripheral edge regions, the discharge channels 32a have a curved peripheral surface 32b.

Although it is contemplated by the inventor that the impeller 10 of the instant disclosure can be formed through joining several independent parts, for example attaching the blades 18 and the rotatable drive attachment region 12 to the hub 14, in preferred embodiments, the blades 18 and/or the rotatable drive attachment region 12 are integrally formed with the hub 14. In more preferred embodiments, the impeller 10 and the various components are formed of a monolithic structure. Furthermore, in some embodiments, a connecting ring 36 is provided for joining each blade or blade ends to the next near the distal end region 26b, as shown in the figures.

Briefly, as noted above, biodegradable and non-biodegradable microcarriers allow cell attachment to a particle that can be left attached to the cell cluster and harvested from the bioreactor once a desired cell confluency is reached. The mass of produced cells and biodegradable microcarriers, in some embodiments, can then be introduced into a patient or biological system without undertaking a microcarrier separation process since the biodegradable microcarriers will dissolve in the patient's body or biological system over a period of time. In the case of the use of non-biodegradable microcarriers a separation step, such as through the use of trypsinization as is known in the field of cell culturing, may be undertaken so a release the cells from the non-biodegradable microcarrier. In some instance it may be also desirable to undertake such a separation step when utilizing biodegradable microcarriers.

Biodegradable and non-biodegradable microcarriers are typically used in small applications as a matrix to grow cell structures, typically epithelial cells, yet in the correct stirring conditions can be used to expand suspension cell cultures of various cell types, such as for example, stem cells or T-cells.

Given some the of the drawbacks noted above, such as increased shear and increased turbulence as a result of the increased culture medium velocities required to maintain the biodegradable microcarriers and non-biodegradable microcarriers having a higher relative density versus $H_2O$ in suspension, using conventional impellers in a bioreactor, observed even in small volume bioreactors such a one-litre and below, an alternative system has been developed which may allow the scale-up of bioreactor suspension cell culturing and ameliorate at some of the drawbacks. Such a system may allow a scale-up to, for example, a fifty-litre suspension cell culturing bioreactor (and beyond), suitable for expanding cell cultures to sizes required for commercial and therapeutic uses. Commercial and therapeutic uses of stem cells is one such arena where scale-up is desirable to meet demand.

Figure 15:
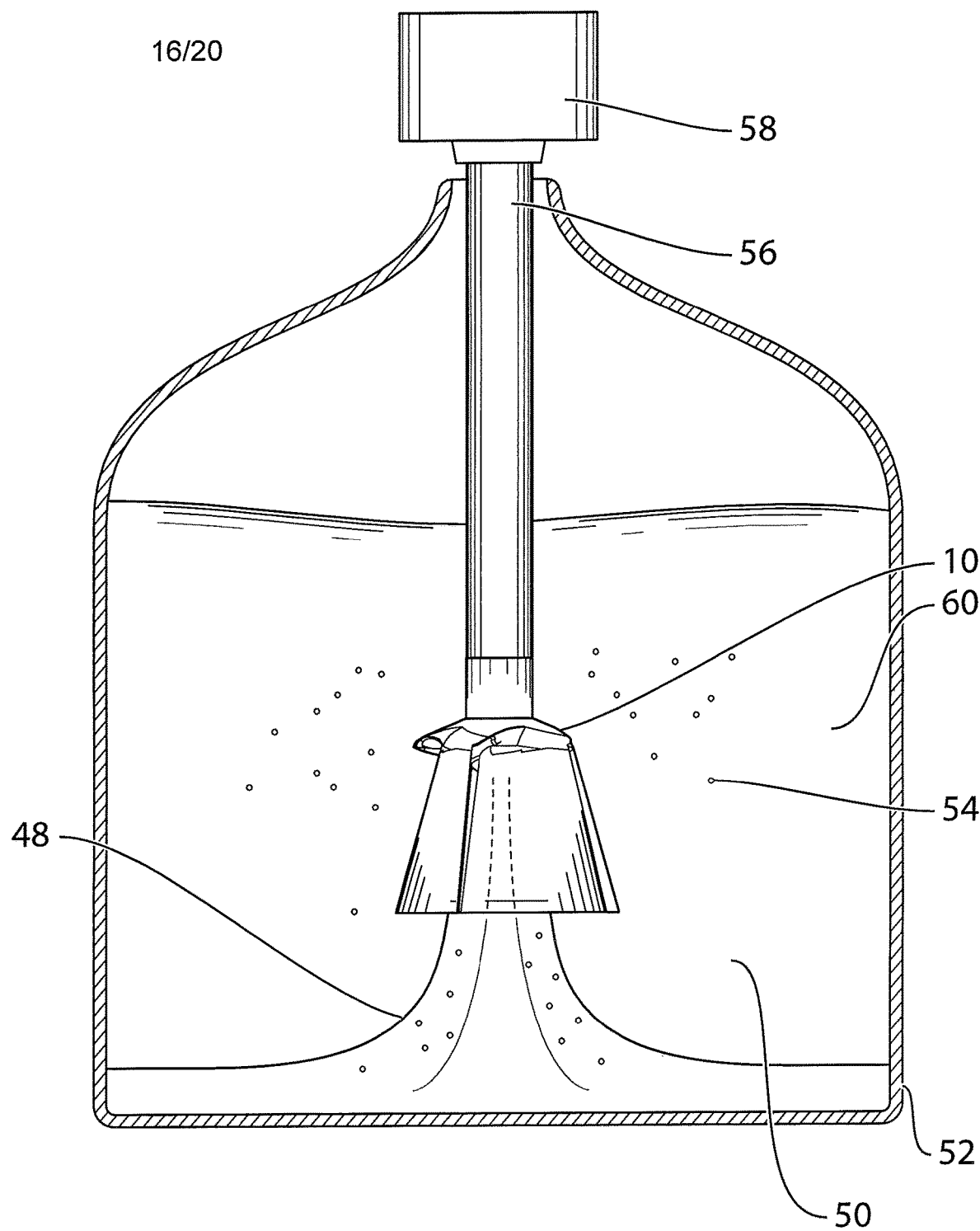
FIG. 15 is a schematic side view of an exemplary cell-culturing bioreactor system maintaining microcarriers in suspension

Turning now to the presently disclosed system and with reference to FIG. 15, there is provided a suspension cell culturing bioreactor 52 suitable for suspension cell culture of various cell types, and in particular embodiments, stem cells. Within the bioreactor 52 is placed a suitable quantity of suitable biodegradable and/or non-biodegradable microcarrier beads 54 such as those commercially available and/or as may be determined by a person of skill in the art as well as a volume of an appropriate cell culture medium and a desired quantity of seed cells (not shown for simplicity). The desired quantity of seed cells may be determined by a person of skill in the art so as to render an expanded suspension cell culture through the use of suspension cell culturing. Disposed within the bioreactor having therein the above-noted cell culture medium, biodegradable microcarrier and/or non-biodegradable microcarrier beads 54, which in some instance may have a relative density versus $H_2O$ similar to biodegradable microcarrier beads, and seed cells is a rotatably-driven impeller, such as impeller 10, designed to impart a swirling motion to the culture medium 60 which can maintain the microcarriers in suspension in a low shear and/or low turbulence environment. The rotatably-driven impeller is driven the coupled impeller drive shaft 56 operatively coupled to motor 58. In some embodiments, the motor 58 may be capable or rotation in both a clock-wise or counter clockwise direction as may be selected by an operator. In some embodiments, the microcarriers, and in particular the non-biodegradable microcarriers may have a relative density versus $H_2O$ of greater than being neutrally buoyant. In preferred embodiments, the biodegradable microcarrier beads and/or non-biodegradable microcarrier beads have a relative density versus $H_2O$ of from about 1.01 $cm^2/g$ to about 1.3 $cm^2/g$. In more preferred embodiments, the biodegradable microcarrier beads and/or non-biodegradable microcarrier beads have a relative density versus $H_2O$ of from about 1.01 $cm^2/g$ to about 1.2 $cm^2/g$. As noted above, such impellers have been disclosed and are described in more detail below, addition to the impeller 10 of the instant application disclosed herein. However, it should be noted that the instant disclosure is not limited to the instantly presented impellers and such are only provided for exemplary purposes so as to better define the invention made and thus presented herein.

EXAMPLES

Example 1

It has been surprising found that when undertaking a separation step of the microcarriers and produce cells, that following trypsinization, reversing the direction of the impeller rotation aids to increase the quantity of recovered cells from the suspension culture. Table 1 below shows an exemplary comparison of harvested viable cells utilizing the impeller 10 in a bioreactor for suspension cell culturing of mesenchymal stem cells compared to using an axial propeller.

TABLE 1

| Harvest Output | Axial Propeller | Impeller 10 |
| --- | --- | --- |
| Total Cells | 1.17E+09 | 1.38E+09 |
| Viable Cells | 1.01E+09 | 1.31E+09 |
| Percent recovered cell viability | 83% | 95% |

In relation to the comparison noted in Table 1, the total number of cells seeded in both the suspension culture mixed with the axial propeller and the impeller 10 as disclosed herein, was 8.64E+07. The harvesting efficiency for both of the impellers was greater than 98%. In reversing the impellers to aid in cell harvesting, the impeller 10 of the instant disclosure showed a more rapid cell detachment, which was observed at 7.5 min. Surprisingly, the number of viable cells harvested from the bioreactor suspension cell culture mixed with impeller 10 was 95% as compared to the number of viable cells harvested from the bioreactor suspension culture mixed with the axial propeller being 83%. Therefore, the suspension culture mixed with the impeller 10 of the instant disclosure showed a 12% increase in number of viable cells recovered over the axial propeller.

Example 2

Figure 16A:
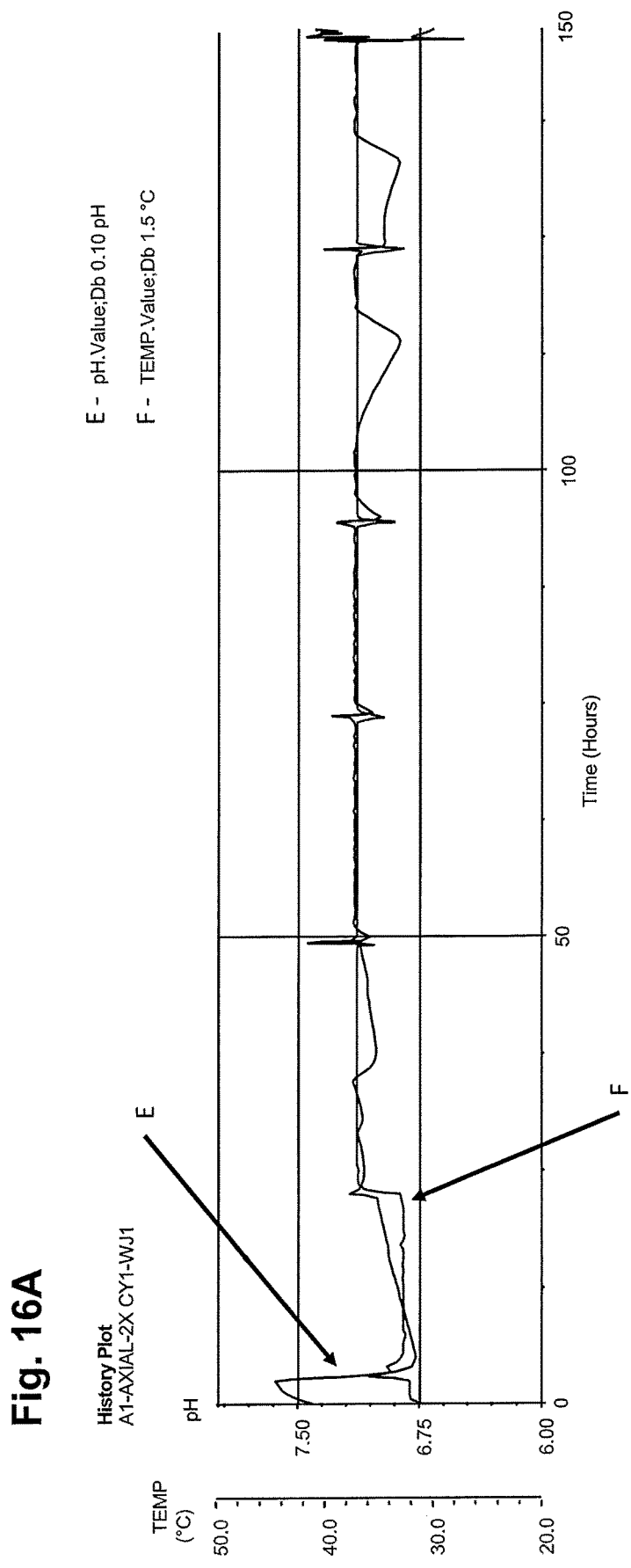
FIG. 16A is a pH and temperature versus time plot of pH and temperature of a culture medium in a bioreactor vessel mixed with an axial propeller.
Figure 16B:
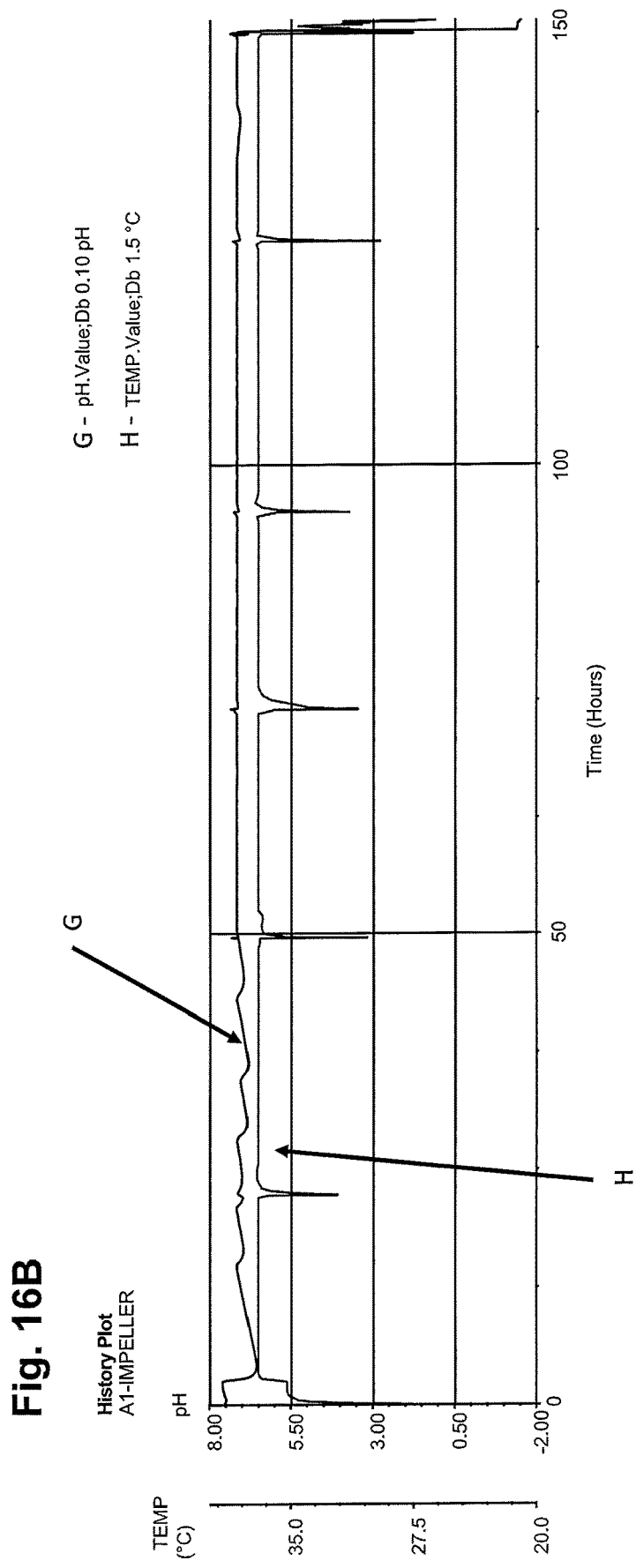
FIG. 16B is a pH and temperature versus time plot of pH and temperature of a culture medium in a bioreactor vessel mixed with an impeller of the instant disclosure.
Figure 17A:
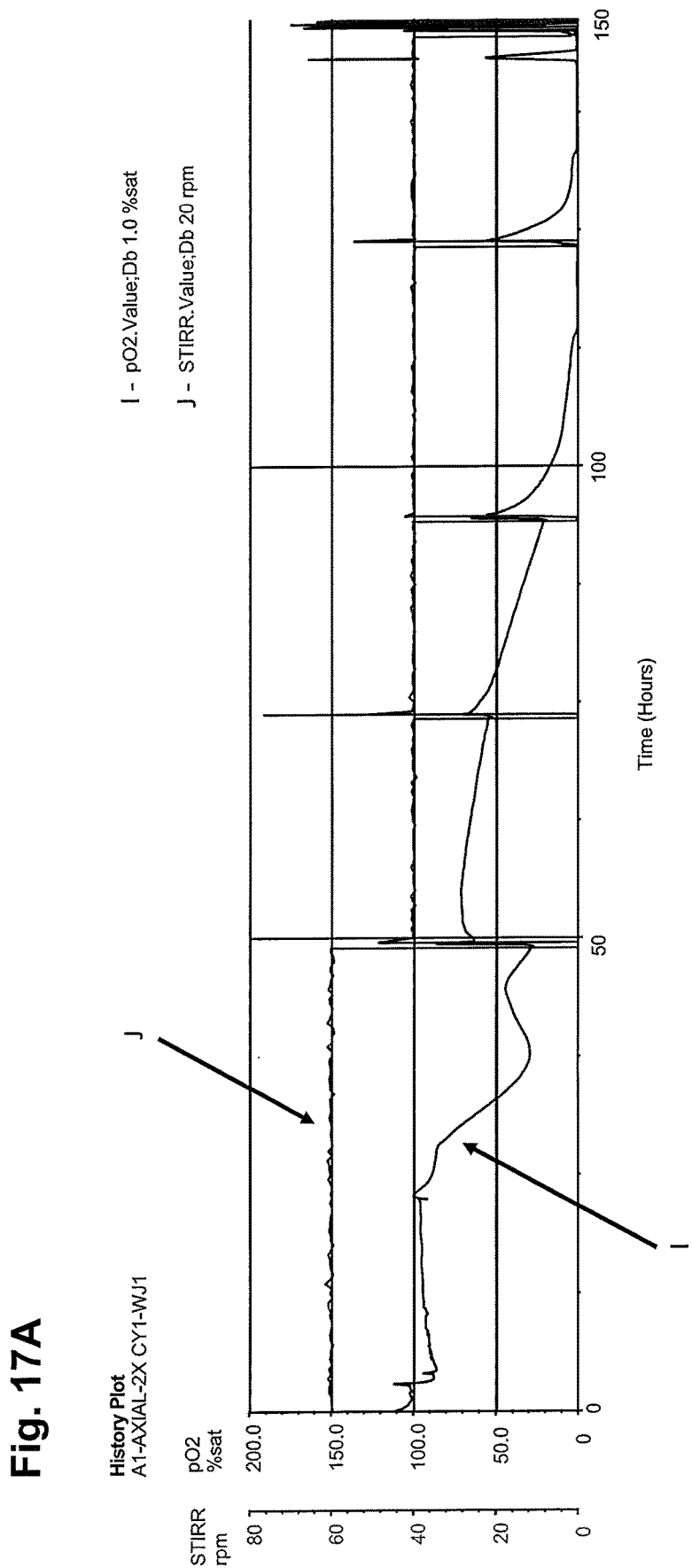
FIG. 17A is a dissolved oxygen ($pO_2$) versus time plot of dissolved oxygen in a culture medium in a bioreactor vessel mixed with an axial propeller.
Figure 17B:
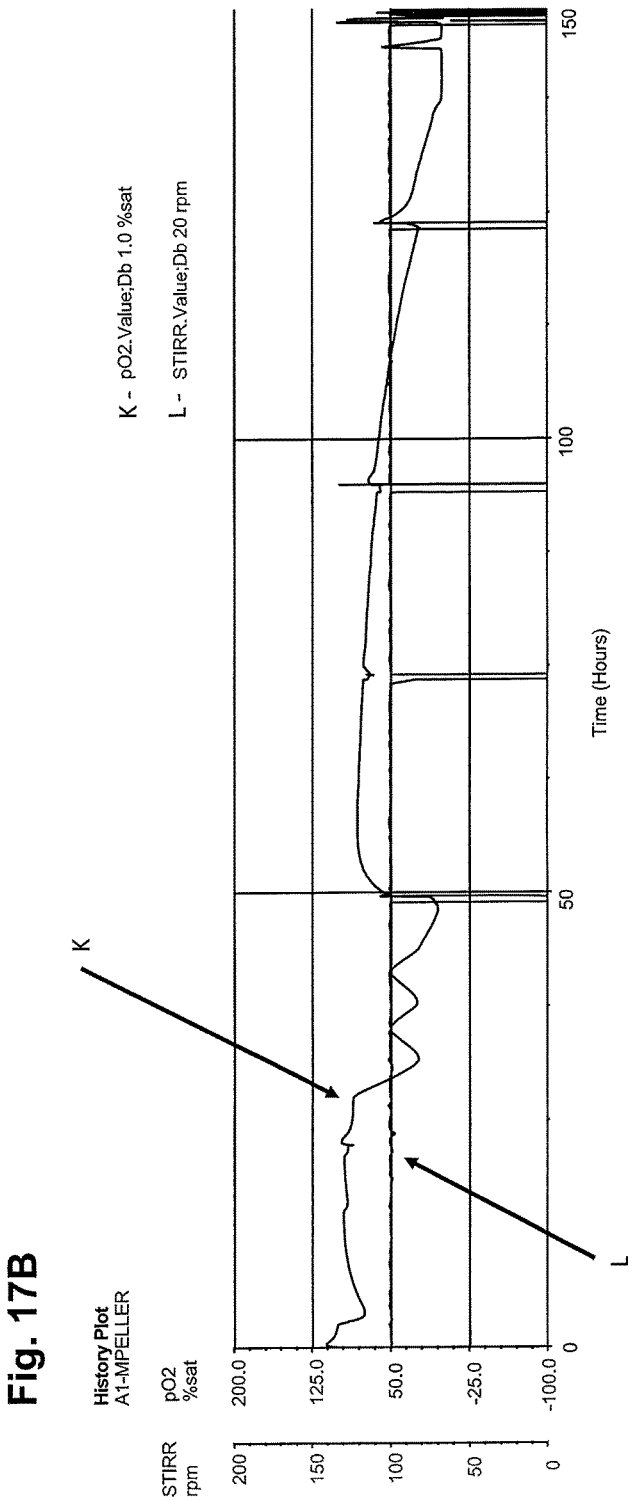
FIG. 17B is a dissolved oxygen ($pO_2$) versus time plot of dissolved oxygen in a culture medium in a bioreactor vessel mixed with an impeller of the instant disclosure.

The impeller 10 of the instant disclosure was compared to an axial propeller in a bioreactor system for suspension culturing in order to determine and compare the pH (element E in FIG. 16A; element G in FIG. 16B) and temperature (element F in FIG. 16A; element H in FIG. 16B) conditions over time in: 1) a bioreactor system wherein the culture media is mixed with an axial propeller, as shown in FIG. 16A; and 2) a bioreactor system wherein the culture media is mixed with an impeller 10 as disclosed herein, as shown in FIG. 16B. In order to similarly compare dissolved oxygen levels ($pO_2$) (element I in FIG. 17A; element K in FIG. 17B) and stirring rpm (element J in FIG. 17A; element L in FIG. 17B) in the culture medium over time, the impeller 10 of the instant disclosure was compared to an axial propeller in a bioreactor system for suspension culturing as shown in FIGS. 17A and 17B. FIG. 17A shows the dissolved oxygen levels over time in relation to a culture medium in a bioreactor mixed with an axial propeller and FIG. 17B shows dissolved oxygen levels over time in relation to a culture medium in a bioreactor mixed with an impeller 10 as disclosed herein. In experiments where the results are shown FIGS. 16A, 16B, 17A and 17B the exemplary were results taken over a 150-hour time period.

Briefly, in the bioreactor wherein the culture medium is mixed with an impeller 10 of the instant disclosure FIGS. 16B and 17B indicate a stabilization of the fluid flow within the bioreactor which results in a more steady state as compared to using an axial propeller, as shown in FIGS. 16A and 17A. After some period of time, the date indicates that all areas of the fluid in the bioreactor mixed with the impeller 10 of the instant disclosure are evenly mixed to a point that there are no regions of the vessel that differ in characteristics from each other, thus indicating a uniform distribution. Unlike data of FIGS. 16A and 17A where an axial flow propeller was used to mix the culture medium, the impeller 10 of the instant disclosure shows a flat line of dissolved oxygen and pH readings, as shown in FIGS. 16B and 17B thereby indicating that all zones of the fluid in motion in the bioreactor have an equal measurement due to a more complete mixing and thus the interior of the bioreactor vessel can be considered one mixing zone. In an axial propeller-mixed bioreactor vessel, readings such as dissolved oxygen and PH, show spikes of high and low during the mixing which indicates that there are several fluid mixing zones.

Suitable conical impellers, in additional to the impeller 10 described in detailed herein, such as those disclosed in U.S. Pat. No. 5,314,310, entitled "SPIDER MOUNTED CENTRIFUGAL MIXING IMPELLER", issued May 24, 1994 (Bachellier, Carl R.), U.S. Pat. No. 5,938,332, entitled "MIXING DEVICE", issued Aug. 17, 1999 (Bachellier, Carl R.) and International Patent Application serial number PCT/CA2012/050873, entitled "IMPROVED IMPELLER APPARATUS AND DISPERSION METHOD FIELD OF THE INVENTION", filed Dec. 5, 2012 (Bachellier, Carl R.), herein incorporated by reference disclose various impellers for mixing fluids which comprise a top hub having a flat interior surface; that is, the inside bottom surface of the hub is perpendicular to the axis of rotation. For example, the bottom surface of the hub, when the impeller is oriented in a vertical plane, is oriented horizontally. During use, when such impellers rotate, an upward spiral helical intake vortex to the fluid is created.

As noted above, although the above-discussed impellers may be suitable for suspension cell culturing utilizing biodegradable microcarriers and/or non-biodegradable microcarriers which may have a relative density versus $H_2O$ of greater than being neutrally buoyant, the invention is not so limited and other existing or future impeller designs may also be suitable in the instantly disclosed system and method. Another consideration, regardless of the impeller design chosen to stir the culture medium 60 is providing a drive shaft 56 for driving the impeller which only partially extends into to the bioreactor. Such a depth may be determined by one of skill in the art, however, a low shear and low turbulence environment may further be enhanced or achieved since a guidance peg on the bottom of the bioreactor vessel, as commonly present in currently available bioreactor designs, which may further cause unwanted fluid disruption or turbulence may not be present or necessary. Thus, the elimination of one or more guidance pegs may allow for smoother, and thus, less turbulent fluid flow of the culture medium in use during the suspension cell culturing.

Furthermore, the instantly disclosed system may enable the suspension cell culturing with biodegradable microcarriers and/or non-biodegradable microcarriers which may have a relative density versus $H_2O$ of greater than being neutrally buoyant in larger scale bioreactors, such as for example, up to and greater than fifty-litre volumes.

In some embodiments, it is also contemplated that the instantly disclosed system may be provided as a complete system in which only seed cells need to be added by an end-user. For example, the system may be provided as a bioreactor, having therein suitable biodegradable and on-biodegradable microcarrier beads, and a suitable drivable impeller operably disposed therein. In practice, an end user may simply add a suitable quantity of desired seed cells and suspension culture medium 60, introduce and maintain the system to a suitable environment and connect a drive shaft 56, connected to the impeller, to a motor 58 and apply a force to cause rotation of the impeller. In some embodiments, such a prepared system may be provided complete with a suitable culture medium preinstalled for a given cell type.

It is to be understood that the above description it is intended to be illustrative, and not restrictive. Many other embodiments will be apparent to those skilled in the art, upon reviewing the above description. The scope of the invention should, therefore, be determined with reference to the appended claims, along with the full scope of equivalents to which such claims are entitled.

Although the present invention has been described with reference to specific exemplary embodiments, it will be evident that various modifications and changes may be made to these embodiments without departing from the broader spirit and scope of the disclosed subject matter as defined by the appended claims.

What is claimed is:

1. An impeller couplable to a rotatable drive by way of a rotatable drive attachment region coupled to a generally circularly shaped hub, said generally circularly shaped hub including a downwardly directed progressively tapered volume having coupled thereto a proximal end region of one or more arced blades, said proximal region arranged on said downwardly directed progressively tapered volume in a spiraling pattern where each of said one or more arced blades has an arc with an increasing radius to said arc towards a peripheral edge region of said hub so as to form a periodic pattern, wherein a number of periods corresponds to the number of blades;

said proximal end region of said one or more increasing radius arced blades extending from said peripheral edge region of said hub along said downwardly directed progressively tapered volume to a predetermined point inward of said peripheral edge region;

said one or more arced blades further being flared as extending from said proximal end region thereof to a remote distal end region such that the distal end region of each of said one or more increasing radius arced blades, in combination, defines a larger circumference than that of said hub, thereby imparting a generally frusto-conical shape to the impeller.

2. The impeller as defined in claim 1, comprising at least two increasing radius arced blades.

3. The impeller as defined in claim 2, further comprising a ring coupled near the distal end regions of said one or more increasing radius arced blades for connecting said one or more radius arced blades.

4. The impeller as defined in claim 3, wherein said ring is integrally formed with said one or more increasing radius arced blades.

5. The impeller as defined in claim 1, wherein said periods formed into said downwardly directed progressively tapered volume comprises a plurality of spiral helices which corresponds the number of increasing radius arced blades.

6. The impeller as defined in claim 5, wherein said one or more increasing radius arced blades extending from said peripheral edge region of said hub along said downwardly directed progressively tapered volume extend from ridges of said spiral helices.

7. The impeller as defined in claim 6, having channels formed intermittent said ridges following said spiral helices so as to form a path continuous with a sequence of distinct conical spiral segments between said one or more increasing radius arced blades.

8. The impeller as defined in claim 7, wherein said channels have a substantially semicircular profile.

9. The impeller as defined in claim 7, said hub having a curved peripheral surface forming a discharge channel located at a peripheral terminus of said spiral helices adjacent each of the one or more arced blade proximal end region extending from said channels.

10. The impeller as defined in claim 5, wherein said spiral helices of the downwardly directed progressively tapered volume is a logarithmic spiral.

11. The impeller as defined in claim 1, wherein said one or more increasing radius arced blades are integrally formed with said hub.

12. The impeller as defined in claim 1, wherein said progressively tapered volume has a compound logarithmic taper.

13. An impeller couplable to a rotatable drive comprising:
a generally circularly shaped hub including a downwardly directed progressively tapered volume having coupled thereto toward a peripheral edge region thereof a proximal end region of one or more arced blades, wherein said one or more arced blades are flared as extending from the proximal end region thereof to a remote distal end region thereof, and said one or more arced blades being arranged on said downwardly directed progressively tapered volume in a spiraling pattern where each of said one or more arced blades has an arc with an increasing radius to said arc towards the peripheral edge region of said hub so as to form a periodic pattern, wherein a number of periods formed into said downwardly directed progressively tapered volume corresponds to the number of the one or more arced blades, and said one more arced blades project generally downwards from said peripheral edge region and to define a periodically flaring impeller radius along their length which allows for tangential fluid flow between adjacent blade ends.

14. The impeller as defined in claim 13, further comprising a ring coupled near the distal end region of said one or more flaring arced blades for connecting said one or more flaring arced blade ends.

15. The impeller as defined in claim 14, wherein said ring is integrally formed with said one or more flaring arced blades.

16. The impeller as defined in claim 13, wherein said one or more arced blades flare in such a manner that the distal end region of each of said one or more arced blades, in combination, defines a larger circumference than that of said hub, thereby imparting a generally frusto-conical shape to the impeller.

* * * * *